US007151082B2

(12) United States Patent
Tracey et al.

(10) Patent No.: US 7,151,082 B2
(45) Date of Patent: Dec. 19, 2006

(54) ANTAGONISTS OF HMG1 FOR TREATING INFLAMMATORY CONDITIONS

(75) Inventors: Kevin J. Tracey, Old Greenwich, CT (US); Haichao Wang, Avenel, NJ (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 522 days.

(21) Appl. No.: 10/300,068

(22) Filed: Nov. 20, 2002

(65) Prior Publication Data

US 2003/0143194 A1   Jul. 31, 2003

Related U.S. Application Data

(60) Continuation-in-part of application No. 10/210,747, filed on Jul. 31, 2002, which is a continuation of application No. 09/503,632, filed on Feb. 14, 2000, now Pat. No. 6,468,533, which is a division of application No. 09/248,574, filed on Feb. 11, 1999, now Pat. No. 6,303,321.

(51) Int. Cl.
  *A61K 38/00*   (2006.01)
  *A61K 39/395*   (2006.01)
  *G01N 33/566*   (2006.01)
  *C07K 1/00*   (2006.01)

(52) U.S. Cl. .................. 514/2; 514/44; 424/130.1; 424/145.1; 436/501; 435/7.1; 530/300; 530/351; 530/387.1; 530/388.22

(58) Field of Classification Search ................ None
  See application file for complete search history.

(56) References Cited

U.S. PATENT DOCUMENTS

| 5,594,114 A | 1/1997 | Goodearl et al. |
| 6,303,321 B1 | 10/2001 | Tracey et al. ............ 435/75.1 |
| 6,448,223 B1 | 9/2002 | Tracey et al. ............ 514/2 |
| 6,468,533 B1 | 10/2002 | Tracey et al. |
| 2003/0017155 A1 | 1/2003 | Tracey et al. |
| 2003/0113323 A1 | 6/2003 | Tracey et al. |
| 2004/0120953 A1 | 6/2004 | Tracey et al. |

FOREIGN PATENT DOCUMENTS

| EP | 1 079 849 B1 | 1/2002 |
| JP | 362166897 A | 1/1986 |
| WO | WO 99/59609 | 11/1999 |
| WO | WO 02/074337 A1 | 9/2002 |
| WO | WO 02/092004 A2 | 11/2002 |
| WO | WO 2004/004763 A2 | 1/2004 |

OTHER PUBLICATIONS

Janis Kuby, Immunology, 1992, p. 1.*
Lotze-MT et al., Nature Reviews 5(331)2005.*
Romani, M., et al., "Serological Analysis of Species Specificity in the High Mobility Group Chromosomal Proteins," *J. Biol. Chem.*, 254(8):2918-2922 (1979).
Bustin, M., et al., "Immunological Relatedness of High Mobility Group Chromosomal Proteins from Calf Thymus," *J. Biol. Chem.*, 253(5):1694-1699 (1978).
Rauvala, H. and Pihlaskari, R., "Isolation and Some Characteristics of an Adhesive Factor of Brain That Enhances Neurite Outgrowth in Central Neurons," *J. Biol. Chem.*, 262(34):16625-16635 (1987).
Daston, M. M. and Ratner, N., " Expression of P30, a Protein with Adhesive Properties, in Schwann Cells and Neurons of the Developing and Regenerating Peripheral Nerve," *J. Cell. Biol.*, 112(6):1229-1239 (1991).
Parkkinen, J., et al., "Amphoterin, the 30-kDa Protein in a Family of HMG1-type Polypeptides," *J. Biol. Chem.*, 268(26):19726-19738 (1993).
Sobajima, J. , et al., "High Mobility Group (HMG) Non-Histone Chromosomal Proteins HMG1 and HMG2 are Significant Target Antigens of Perinuclear Anti-Neutrophil Cytoplasmic Antibodies in Autoimmune Hepatitis," *Gut*, 44:867-873 (1999).
Ma W., et al., "Detection of Anti-Neutrophil Cytoplasmic Antibodies in MRL/Mp-*lpr/lpr* Mice and Analysis of their Target Antigens," *Autoimmunity*, 32(4):281-291 (2000).
Banks, G. C., et al., "The HMG-I(Y) A·T-hook Peptide Motif Confers DNA-binding Specificity to a Structured Chimeric Protein," *J. Biol. Chem.*, 274(23):16536-16544 (1999).
Scaffidi, P., et al., "Release of Chromatin Protein HMGB1 by Necrotic Cells Triggers Inflammation," *Nature*, 418:191-195 (2002).
Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J. Protein Chem.*, 11(5):433-444 (1992).
Colman, P. M., "Effects of Amino Acid Sequence Chamges on Antibody-Antigen Interactions," *Res. Immunol.*, 145(1):33-36 (1994).
Freeman, B. D., et al., "The Role of Inflammation in Sepsis and Septic Shock: A Meta-Analysis of Both Clinical and Preclinical Trials of Anti-Inflammatory Therapies," in *Inflammation: Basic Principals and Clinical Correlates* (John I. Gallin and Ralph Snyderman eds., Lippincott, Williams & Wilkins, Philadelphia, 3$^{rd}$ ed. 1999), pp. 965-975.
Lederman, S., et al., "A Single Amino Acid Substitution in a Common African Allele of the CD4 Molecule Ablates Binding of the Monoclonal Antibody OKT," *Mol. Immunol.*, 28(11):1171-1181 (1991).

(Continued)

*Primary Examiner*—Janet L. Andres
*Assistant Examiner*—Michael Brannock
(74) *Attorney, Agent, or Firm*—Hamilton, Brook, Smith & Reynolds, P.C.

(57) ABSTRACT

There is disclosed a pharmaceutical composition and method for treating sepsis, including septic shock and ARDS (acute respiratory distress syndrome), comprising administering an effective amount of a HMG1 antagonist. There is further disclosed a diagnostic method for monitoring the severity or potential lethality of sepsis or septic shock, comprising measuring the serum concentration of HMG1 in a patient exhibiting or at risk or exhibit sepsis or septic shock symptoms. Lastly, there is disclosed a pharmaceutical composition and method for effecting weight loss or treating obesity, comprising administering an effective amount of HMG1 or a therapeutically active HMG1 fragment.

19 Claims, 12 Drawing Sheets

OTHER PUBLICATIONS

Czura, C., et al., "Dual Roles for HMGB1: DNA Binding and Cytokine," *J. Endotoxin Res.*, 7(4):315-321 (2001).

Wen, L., et al., "A Human Placental cDNA Clone that Encodes Nonhistone Chromosomal Protein HMG-1," *Nucleic Acids Res.*, 17(3):1197-1213 (1989).

Uesugi, H., et al., "Prevalence and Characterization of Novel pANCA, Antibodies to the High Mobility Group Non-Histone Chromosomal Proteins HMG1 and HMG2, in Systemic Rheumatic Diseases," *J. Rheumatol.*, 25(4):703-709 (1998).

Passalacqua, M., et al., "Stimulated Astrocytes Release High-Mobility Group 1 Protein, an Inducer of Lan-5 Neuroblastoma Cell Differentiation," *Neuroscience*, 82(4):1021-1028 (1998).

Chou, D. K. H., et al., "Identity of Nuclear High-Mobility-Group Protein, HMG-1, and Sulfoglucuronyl Carbohydrate-Binding Protein, SBP-1, in Brain," *J. Neurochem.*, 77:120-131 (2001).

Imamura, T., et al., "Interaction with p53 Enhances Binding of Cisplatin-Modified DNA by High Mobility Group 1 Protein," *J. Biol. Chem.*, 276(10):7534-7540 (2001).

Ise, T., et al., "Transcription Factor Y-Box Binding Protein 1 Binds Preferentially to Cisplatin-Modified DNA and Interacts With Proliferating Cell Nuclear Antigen," *Cancer Res.*, 59:342-346 (1999).

Jung, F., et al., "Antibodies Against a Peptide Sequence Located in the Linker Region of the HMG-1/2 Box Domains in Sera From Patients With Juvenile Rheumatoid Arthritis," *Arthritis Rheum.*, 40(10):1803-1809 (1997).

Bianchi, M. E., et al., "Specific Recognition of Cruciform DNA by Nuclear Protein HMG1," *Science*, 243:1056-1059 (1989).

Suda, T., et al., "A Novel Activity of HMG Domains: Promotion of the Triple-Stranded Complex Formation Between DNA Containing $(GGA/TCC0)_{11}$ and $d(GGA)_{11}$ Oligonucleotides," *Nucleic Acids Res.*, 24(23):4733-4740 (1996).

Ayer, L. M., et al., "Antibodies to HMG Proteins in Patients With Drug-Induced Autoimmunity," *Arthritis Rheum.*, 37(1):98-103 (1994).

Rauvala, H., et al., "The Adhesive and Neurite-Promotin Molecule p30: Analysis of the Amino-Terminal Sequence and Production of Antipeptide Antibodies That Detect p30 at the Surface of Neuroblastoma Cells and of Brain Neurons," *J. Cell Biol.*, 107(6):2293-2305 (1988).

Sobajima, J., et al., "Prevalence and Characterization of Perinuclear Anti-Neutrophil Cytoplasmic Antibodies (P-ANCA) Directed Against HMG1 and HMG2 in Ulcerative Colitis (UC)," *Clin. Exp. Immunol.*, 111:402-407 (1998).

Yamada, S., et al., "High Mobility Group Protein 1 (HMGB1) Quantified by ELISA With a Monoclonal Antibody That Does Not Cross-React With HMGB2," *Clin. Chem.*, 49(9):1535-1537 (2003).

Falciola, L., et al., "High Mobility Group 1 Protein is Not Stably Associated with the Chromosomes of Somatic Cells," *J. Cell Biol.*, 137 (1):19-26 (1997).

Vanderbilt, J.N., et al., "Monoclonal Antibodies as Probes for the Complexity, Phylogency, and Chromatin Distribution of High Mobility Group Chromosomal Proteins 1 and 2," *J. Biol. Chem.*, 260(16) :9336-9345 (1985).

Bustin, M., et al., "Antigenic Determinants of High Mobility Group Chromosomal Proteins 1 and 2," *Biochem.*, 21 : 6773-6777 (1982).

Tsuneoka, M., et al., "Monoclonal Antibody Against Non-Histone Chromosomal Protein High Mobility Group 1 Co-Migrates With High Mobility Group 1 Into the Nucleus," *J. Biol. Chem.*, 261(4):1829-1834 (1986).

Zhang, M. et al., "Tumor Necrosis Factor", in *The Cytokine Handbook*, (Academic Press Limited), Third Edition, pp. 517-547 (1998).

Johns, E.W., et al. "History, Definitions and Problems", in *The HMG Chromosomal Problems*, (Academic Press), London: Chapter 1, pp. 1-7 (1982).

Landsman, D., et al., "A Signature for the HMG-1 Box DNA-Binding Proteins", *BioEssays*, 15(8) : 539-546 (1993).

Baxevanis, A.D., et al., "The HMG-1 Box Protein Family: Classification and Functional Relationships", *Nucleic Acids Res.*, 23(9) :1604-1613 (1995).

Merenmies, J., et al., "30-kDa Heparin-Binding Protein of Brain (Amphoterin) Involved in Neurite Outgrowth", *J. Biol. Chem.*, 266 (25) : 16722-16729 (1991).

Milev, P., et al., "High Affinity Binding and Overlapping Localization of Neurocan and Phosphacan/Protein-Tyrosine Phosphatase—ζ/β with Tenascine -4, Amphoterine, and the Heparin-Binding Growth-Associated Molecule", *J. Biol. Chem.*, 273(12) :6998-7005 (1998).

Salmivirta, M., et al., "Neurite Growth-Promoting Protein (Amphoterin, p. 30) Binds Syndecan", *Exp. Cell Res.*, 200: 444-451 (1992).

Melloni, E., et al., "Identity in Molecular Structure Between "Differentiation Enhancing Factor" of Murine Erithroleukemia Cells and the 30 kD Heparin-Binding Protein of Developing Rat Brain", *Biochemical and Biophysical Research Communications*, 210(1): (1995).

Melloni, E., et al., "Extracellular Release of the 'Differentiation Enhancing Factor', and a HMG1 Protein Type, is an Early Step in mUrine Erythroluekemia Cell Differentiation", *FEBS Lett.*, 368: 466-470 (1995).

Mohan, P.S., et al., "Sulfoglycolipids Bind to Adhesive Protein Amphoterin (p30) in the Nervous System", *Biochemical and Biophysical Research Communications*, 182(2) (1992).

Yamawaki, M., et al., "Generation and Characterization of Anti-Sulfoglucuronosyl Paragloboside Monoclonal Antibody NGR50 and its Immunoreactivity with Peripheral Nerve", *J. Neurosci. Res.*, 44: 586-593 (1996).

Vassalli, J., et al., "The Plasminogen Activator/Plasmin System", *J. Clin. Invest.*, 88: 1067-1072 (1991).

Parkkinen, J., et al., "Interactions of Plasminogen and Tissue Plasminogen Activator (t-PA) with Amphoterin", *J. Biol. Chem.*, 266(25) :16730-16735 (1991).

Redlitz, A., et al., "Receptors for Plasminogen and t-PA: An Update", *Baillière's Clinical Haemtology*, 8(2): 313-327 (1995).

Sobajima, J., et al., "Novel autoantigens of perinuclear anti-neutrophil cytoplasmic antibodies (P-ANCA) in ulcerative colitia: non-histone chromosomal proteins, HMG1 and HMG2" *Clin. Exp. Immunol.* , 107: 135-140 (1997).

Sobajima, J., et al., "Anti-neutrophil cytopasmic antibodies (ANCA) in ulcerative colitis: anti-cathespin G and a novel antibody correlate with a refractory type," *Clin. Exp. Immunol.*, 105:120-124 (1996).

Sparatore, B., et al., "Extracellular high-mobility group 1 protein is essential for murine erythroleukaemia cell differentiation," *Biochem. J.*, 320:253-256 (1996).

Tomita, N., et al., "Direct In Vivo Gene Introduction Into Rat Kidney," *Biochemical and Biophysical Research Communications* 186(1):129-134 (1992).

Wang, H., et al., "HMG-1 as a Late Mediator of Endotoxin Lethality in Mice," *Science* 285:248-251 (1999).

Abraham, E., et al., "Cutting Edge: HMG-1 as a Mediator of Acute Lung Inflammation," *J. Immunol.*, 165:2950-2954 (2000).

Andersson, U., et al., "High Mobility Group 1 Protein (HMG-1) Stimulates Proinflammatory Cytokine Synthesis in Human Monocytes," *J. Exp. Med.*, 192:565-570 (2000).

Bianchi, M.E., et al., "The DNA Binding Site of HMG1 Protein is Composed of Two Similar Segements (HMG Boxes), Both of Which Have Counterparts in Other Eukaryotic Regulatory Proteins," *The EMBO Journal*, 11(3): 1055-1063 (1992).

Bustin, M. "Revised Nomenclature for High Mobility Group (HMG) Chromosomal Proteins," *Trends Biochem. Sci.*, 26:152-153 (2001).

Degryse, B., et al., "The High Mobility Group (HMG) Boxes of the Nuclear Protein HMG1 Induce Chemotaxis and Cytoskeleton Reorganization in Rat Smooth Muscle Cells," *J. Cell Biol.*, 152:1197-1203 (2001).

Wang, H., et al., "Proinflammatory Cytokines (Tumor Necrosis Factor and Interleukin 1) Stimulate Release of High Mobility Group Protein-1 by Pituicytes," *Surgery*, 126:389-392 (1999).

U.S. Appl. No. 10/242,056, by Kevin J. Tracey and Haichao Wang, filed Sep. 11, 2002.

U.S. Appl. No. 10/300,072, by Kevin J. Tracey, Huan Yang, Howland Shaw Warren, Jr., and Mitchell P. Fink, filed Nov. 20, 2002.

U.S. Appl. No. 10/210,747, by Kevin J. Tracey and Haichao Wang, filed Jul. 31, 2002.

U.S. Appl. No. 10/719,150, by Kevin J. Tracey and Haichao Wang, filed Nov. 21, 2003.

Benjamini, E. et al., *Immunology: A Short Course*, 2nd ed. (New York, A John Wiley & Sons, Inc.) 1991, p. 40.

Dorland's Illustrated Medical Dictionary, 28th ed. (Philadelphia, W.B. Saunders Co.), 1994, p. 269.

Stedman's Medical Dictionary, 26th ed. (Baltimore, Williams & Wilkins) 1995, p. 283.

HSTAT, Health Services/Technology Assessment Test. AHRQ Evidence Reports, No. 83, "Effect of Supplemental Antioxidants Vitamin C, Vitamin E, and Coenzyme Q10 for the Prevention and Treatment of Cardiovascular Disease," [online] [retrieved on Feb. 6, 2006]. Retrieved from the Internet: <URL:http://www.ncbi.nlm.nih.gov/entrez/query.fcgi?cmd> p. 1/11-3/11.

Meldrum, D.R., "Tumor Necrosis Factor in the Heart," *Am. J. Physiol.* 274: R577-R595 (1998).

Kalinina, N., et al., "Increased Expression of the DNA-Binding Cytokine HMGB1 in Human Atherosclerotic Lesions: Role of Activated Macrophages and Cytokines," *Arterioscler. Thromb. Vasc. Biol.*, 24: 2320-2325 (2004).

Fiuza, C., et al. "Inflammation-Promoting Activity of HMGB1 on Human Microvascular Endothelial Cells," *Blood*: 101(7): 2652-2660 (2003).

Goldstein, R.S., et al. "HMGB1 Detection in Patients with Cerebral and Myocardial Ischemia," *J. Invest. Med.*, 53(2): S387 (2005) (Abstract From Joint Annual Meeting of the Central-Society-for-Clinical-Research/Midwestern American-Federation-for-Medical-Research).

Østerud, B., et al. "Role of Monocytes in Atherogenesis," *Physiol. Rev.* 83(4):1069-1112 (2003).

Ombrellino, M., et al. "Increased Serum Concentrations of High-Mobility-Group Protein 1 in Haemorrhagic Shock," *Lancet*, 354 (9188):1446-1447 (1999).

* cited by examiner

ANTAGONISTS OF HMG1 FOR TREATING INFLAMMATORY CONDITIONS

RELATED APPLICATIONS

This application is a continuation-in-part of U.S. application Ser. No. 10/210,747, filed Jul. 31, 2002, which is a continuation of U.S. application Ser. No. 09/503,632, filed Feb. 14, 2000, now issued as U.S. Pat. No. 6,468,533, which is a divisional of U.S. application Ser. No. 09/248,574, filed Feb. 11, 1999, now issued as U.S. Pat. No. 6,303,321. The entire teachings of the above applications are incorporated herein by reference.

TECHNICAL FIELD OF THE INVENTION

The present invention provides a pharmaceutical composition and method for treating diseases characterized by activation of an inflammatory cytokine cascade, particularly sepsis, including septic shock and ARDS (acute respiratory distress syndrome), comprising administering an effective amount of an antagonist to the high mobility group 1 protein (HMG1). The present invention further provides a diagnostic method for monitoring the severity of sepsis and related conditions, comprising measuring the serum concentration of HMG1 in a patient exhibiting symptoms of a disease characterized by activation of inflammatory cytokine cascade. Lastly, the present invention provides a pharmaceutical composition and method for effecting weight loss or treating obesity, comprising administering an effective amount of an HMG1 protein or a therapeutically active fragment of the gene product of an HMG1 gene.

BACKGROUND OF THE INVENTION

Sepsis is an often fatal clinical syndrome that develops after infection or injury. Sepsis is the most frequent cause of mortality in hospitalized patients. Experimental models of gram negative sepsis based on administration of bacterial endotoxin (lipopolysaccharide, LPS) have led to an improved understanding of the pathogenic mechanisms of lethal sepsis and conditions related to sepsis by virtue of the activation of a common underlying inflammatory cytokine cascade. This cascade of host-response mediators includes TNF, IL-1, PAF and other macrophage-derived factors that have been widely studied as acute, early mediators of eventual lethality in severe endotoxemia (Zhang and Tracey, In *The Cytokine Handbook*, 3rd ed. Ed. Thompson (Academic Press Limited, USA). 515–547,1998).

Unfortunately, therapeutic approaches based on inhibiting these individual "early" mediators of endotoxemia have met with only limited success in large prospective clinical trials against sepsis in human patients. It is possible to infer from these disappointing results that later-appearing factors in the host response might critically determine pathogenesis and/or lethality in sepsis and related disorders. Accordingly, there is a need to discover such putative "late" mediators necessary and/or sufficient for part or all of the extensive multisystem pathogenesis, or for the lethality, of severe endotoxemia, particularly as endotoxemia is representative of clinical sepsis and related clinical disorders.

HMG1 is a 30 kDa chromosomal nucleoprotein belonging to the burgeoning high mobility group (HMG) of non-histone chromatin-associated proteins. As a group, the HMG proteins recognize unique DNA structures and have been implicated in diverse cellular functions, including determination of nucleosome structure and stability, as well as in transcription and/or replication. The HMG proteins were first characterized by Johns and Goodwin as chromatin components with a high electrophoretic mobility in polyacrylamide gels (see in *The HMG Chromosomal Proteins*, E. W. Johns, Academic Press, London, 1982). Higher eukaryotes exhibit three families of HMG proteins: the HMG-1/-2 family, the HMG-14/-17 family and the HMG-I/-Y family. Although the families are distinguishable by size and DNA-binding properties, they are similar in their physical properties. HMG proteins are highly conserved across species, ubiquitously distributed and highly abundant, and are extractable from chromatin in 0.35 M NaCl and are soluble in 5% perchloric or trichlioroacetic acid. Generally, HMG proteins are thought to bend DNA and facilitate binding of various transcription factors to their cognate sequences, including for instance, progesterone receptor, estrogen receptor, HOX proteins, and Oct1, Oct2 and Oct6. Recently, it has become apparent that a large, highly diverse group of proteins including several transcription factors and other DNA-interacting proteins, contain one or more regions similar to HMG1, and this feature has come to be known as the HMG1 box or HMG1 domain. cDNAs coding for HMG1 have been cloned from human, rat, trout, hamster, pig and calf cells, and HMG1 is believed to be abundant in all vertebrate cell nuclei. The protein is highly conserved with interspecies sequence identities in the 80% range. In chromatin, HMG1 binds to linker DNA between nucleosomes and to a variety of non-β-DNA structures such as palindromes, cruciforms and stem-loop structures, as well as cisplatin-modified DNA. DNA binding by HMG1 is generally believed to be sequence insensitive. HMG1 is most frequently prepared from washed nuclei or chromatin, but the protein has also been detected in the cytoplasm. (Reviewed in Landsman and Bustin, *BioEssays* 15:539–546, 1993; Baxevanis and Landsman, *Nucleic Acids Research* 23:514–523, 1995). To date, no link has been established between the HMG proteins and any clinical condition or disease.

HMG1 has been alternatively identified as a heparin-binding protein abundantly expressed in developing brain and dubbed "amphoterin" for its highly dipolar sequence, comprising two internal repeats of a positively charged domain of about 80 amino acids (the HMG1 box) and an acidic C-terminal domain containing a stretch of approximately 30 continuous glutamic or aspartic acid residues. Amphoterin/HMG1 has been localized to the outer surface of the plasma membranes of epithelial, and especially neuronal cells, where it has been specifically localized to the filipodia of neural cells. Inhibition studies have suggested that amphoterin/HMG1 is required for process (neurite) extension and amphoterin/HGM1 also may be involved in neuron-glia interactions (Meremnies et al., *J. Biol. Chem.* 266:16722–16729,1991; Merenmies et al., *J Biol. Chem.* 266:16722–16729, 1991; Milev et al., *J Biol. Chem.* 273: 6998–7005, 1998; and Salmivirta et al., *Exp. Cell Res.* 200:444–451, 1992). Amphotelin/HMG1 can be released from murine erythroleukemia cells after stimulation with the chemical inducer hexamethylenebisacetamide (Melloni et al., *Biochem. Biophys. Res. Commun.* 210:82–89, 1995). Previous study suggested that the gene product of the HMG1 gene functions as a differentiation enhancing factor by stimulating α-PKC (Melloni et al., *Biochem. Biophys. Res. Commun.* 210:82–89, 1995; and Melloni et al., *FEBS Lett.* 368:466–470, 1995).

The HMG1 gene product has been shown to interact with plasminogen and tissue-type plasminogen activator (t-PA) and effectively enhance plasmin generation at the cell surface, a system that is known to play a role in extracellular proteolysis during cell invasion and tissue remodeling. Amphoterin/HMG1 has also been shown to interact with the receptor of advanced glycosylation end products (RAGE) (Mohan et al., *Biochem. Biophys. Res. Commun.* 182:689–696, 1992; Yamawaki et al., *J. Neurosci. Res.* 44:586–593, 1996; Salmivirta et al., *Exp. Cell Res.* 200: 444–451, 1992; and Vassalli et al., *J. Clin. Invest.* 88:1067–1072, 1991), (Redlitz and Plow, *Baillieres Clin. Haematol.* 8:313–327, 1995; and Parkkinen et al., *J. Biol. Chem.* 266:16730–16735, 1991).

There is a longstanding need in the art to discover improved agents that can prevent the cytokine-mediated inflammatory cascade and have therapeutic activity in a large variety of cytokine-mediated inflammatory diseases. The present invention was made during the course of investigative research to identify agents that mediate toxicity, pathogenesis and/or lethality in sepsis and other disorders related by a common activation of the inflammatory cytokine cascade.

Diseases and conditions mediated by the inflammatory cytokine cascade are numerous. Such conditions include the following grouped in disease categories:

Systemic Inflammatory Response Syndrome, which includes:
  Sepsis syndrome
    Gram positive sepsis
    Gram negative sepsis
    Culture negative sepsis
    Fungal sepsis
    Neutropenic fever
    Urosepsis
  Meningococcemia
  Trauma hemorrhage
  Hums
  Ionizing radiation exposure
  Acute pancreatitis
  Adult respiratory distress syndrome (ARDS)
Reperfusion Injury, which includes
  Post-pump syndrome
  Ischemia-reperfusion injury
Cardiovascular Disease, which includes
  Cardiac stun syndrome
  Myocardial infarction
  Congestive heart failure
Infectious Disease, which includes
  HIV infection/HIV neuropathy
  Meningitis
  Hepatitis
  Septic arthritis
  Peritonitis
  *Pneumonia Epiglottitis*
  *E. coli* 0157:H7
  Hemolytic uremic syndrome/thrombolytic tbrombocytopcnic purpura
  Malaria
  Dengue hemorrhagic fever
  Leishmaniasis
  Leprosy
  Toxic shock syndrome
  *Streptococcal myositis*
  Gas gangrene
    *Mycobacterium tuberculosis*
    *Mycobaclerium aviun intracellulare*
    *Pneumocystis carinii pneumonia*
  Pelvic inflammatory disease
  Orchitis/epidydimitis
  Legionella
  Lyme disease
  Influenza A
  Epstein-Barr Virus
  Viral associated hemiaphagocytic syndrome
  Viral encephalitis/aseptic meningitis
Obstetrics/Gynecology, including:
  Premature labor
  Miscarriage
  Infertility
Inflammatory Disease/Autoimmunity, which includes:
  Rheumatoid arthritis/seronegative arthropathies
  Osteoarthritis
  Inflammatory bowel disease
  Systemic lupus erythematosis
  Iridoeyelitis/uveitistoptic neuritis
  Idiopathic pulmonary fibrosis
  Systemic vasculitis/Wegener's gramilornatosis
  Sarcoidosis
  Orchitis/vasectomy reversal procedures
Allergic/Atopic Diseases, which includes:
  Asthma
  Allergic rhinitis
  Eczema
  Allergic contact dermatitis
  Allergic conjunctivitis
  Hypersensitivity pneumonitis
Malignancy, which includes:
  ALL
  AML
  CML
  CLL
  Hodgkin's disease, non-Hodgkin's lymphoma
  Kaposi's sarcoma
  Colorectal carcinoma
  Nasopharyngeal carcinoma
  Malignant histiocytosis
  Paraneoplastic syndrome/hypercalcemia of malignancy
Transplants, including:
  Organ transplant rejection
  Graft-versus-host disease
Cachexia
Congenital, which includes:
  Cystic fibrosis
    Familial hematophagocytic lymphohistiocytosis
    Sickle cell anemia
Dermatologic, which includes:
  Psoriasis
  Alopecia
Neurologic, which includes:
  Multiple sclerosis
  Migraine headache
Renal, which includes:
  Nephrotic syndrome
  Hemodialysis
  Uremia
Toxicity, which includes:
  OKT3 therapy
  Anti-CD3 therapy
  Cytokine therapy
  Chemotherapy
  Radiation therapy
  Chronic salicylate intoxication
Metabolic/Idiopathic, which includes:
  Wilson's disease
  Hemachromatosis
  Alpha-1 antitrypsin deficiency Diabetes
Hashimoto's thyroiditis
Osteoporosis
Hypothalamic-pituitary-adrenal axis evaluation
Primary biliary cirrhosis

SUMMARY OF THE INVENTION

The present invention provides a pharmaceutical composition for treating conditions (diseases) mediated by the inflammatory cytokine cascade, comprising an effective amount of an antagonist or inhibitor of HMG1. Preferably, the HMG1 antagonist is selected from the group consisting of antibodies that bind to an HMG1 protein, HMG1 gene antisense sequences and HMG1 receptor antagonists. The present invention provides a method for treating a condition mediated by the inflammatory cytokine cascade, comprising administering an effective amount of an HMG1 antagonist. In another embodiment, the inventive method further comprises administering a second agent in combination with the HMG1 antagonist, wherein the second agent is an antagonist of an early sepsis mediator, such as TNF, IL-1α, IL-1β, MIF or IL-6. Most preferably, the second agent is an antibody to TNF or an IL-1 receptor antagonist (IL-1ra).

The present invention further provides a diagnostic and prognostic method for monitoring the severity and predicting the likely clinical course of sepsis and related conditions for a patient exhibiting shock-like symptoms or at risk to exhibit symptoms associated with conditions mediated by the inflammatory cascade. The inventive diagnostic and prognostic method comprises measuring the concentration of HMG1 in a sample, preferably a serum sample, and comparing that concentration to a standard for HMG1 representative of a normal concentration range of HMG1 in a like sample, whereby higher levels of HMG1 are indicative of poor prognosis or the likelihood of toxic reactions. The diagnostic method may also be applied to other tissue or fluid compartments such as cerebrospinal fluid or urine. Lastly, the present invention provides a pharmaceutical composition and method for effecting weight loss or treating obesity, comprising administering an effective amount of HMG1 or a therapeutically active fragment thereof.

BRIEF DESCRIPTION OF THE DRAWINGS

FIG. 1 shows two graphs that profile the induction of HMG1 release by LPS in vitro (FIG. 1A) and in vivo (FIG. 1B). Specifically.

FIG. 2 illustrates that HMG1 is a mediator of pathogenesis and lethality in endotoxemia.

FIG. 3 shows that HMG1 induced TNF release both in vitro (FIG. 3A) and in vivo (FIG. 3B). Specifically, FIG. 3A shows the mean ±S.E.M. of the induced TNP response in two experiments (in triplicate).

FIG. 4 shows the mean ±S.E.M. of net body weight change of three mice per group.

DETAILED DESCRIPTION OF THE INVENTION

Figure 1A:
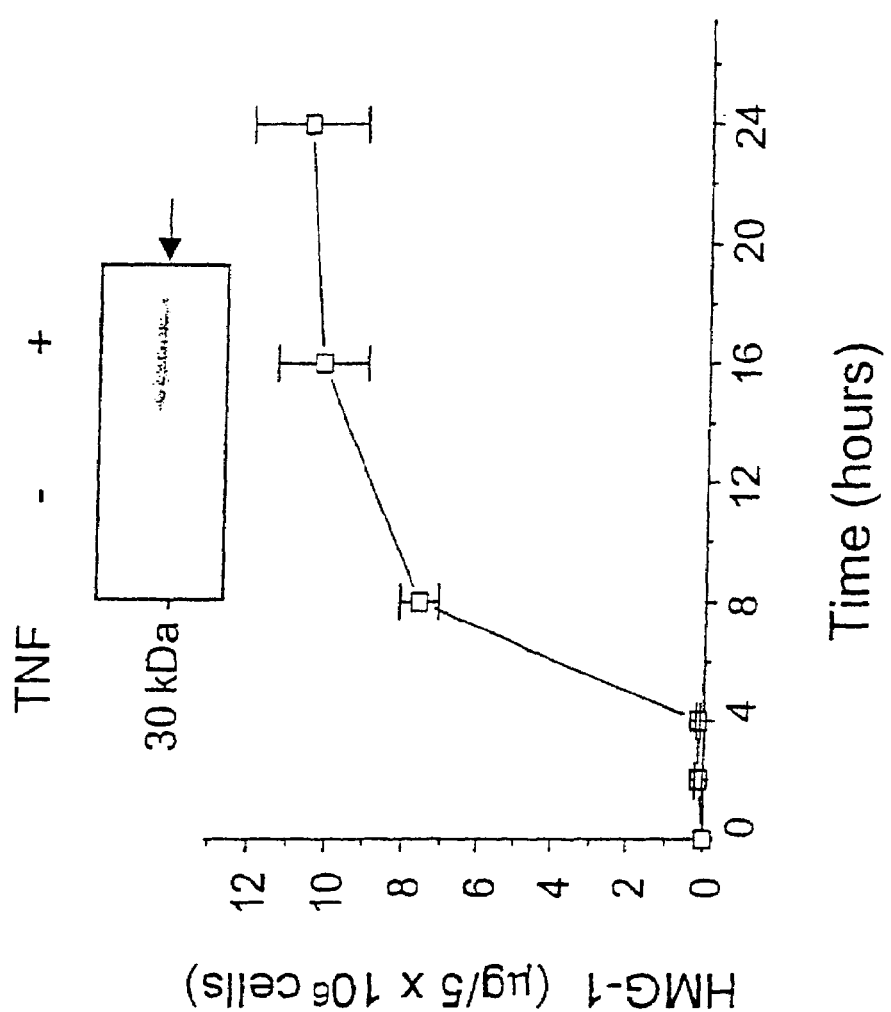
FIG. 1A shows the accumulation of HMG1 in culture supernatants of macrophage RAW 264.7 cells after stimulation with LPS (100 ng/ml). The inset is a Western blot (using antibodies raised against recombinant HMG1) showing induction of HMG1 release from RAW 264.7 cells after induction with TNF.

The present invention is based upon the discovery and isolation of a highly inducible 30 kDa protein that is released by, and accumulates in media conditioned by, cultured murine macrophage-like cells (RAW 264.7) following stimulation with LPS, TNF, or IL-1. A partial amino acid sequence of this isolated polypeptide was identical to the sequence of the HMG1 protein, also known as amphoterin, a protein not before linked to the pathogenesis of any disease. This information was used to clone a cDNA encoding HMG1, which sequence was expressed to provide recombinant protein, which protein was used to generate specific anti-HMG1 antibodies.

Therapeutic and diagnostic efficacy was determined in a series of predictive in vitro and in vivo experiments. The experiments are detailed in the Examples section. For example, following administration of endotoxin ($LD_{100}$) to mice, serum HMG1 levels increased later (at 16 h) than well-known "early" mediators of sepsis (such as TNF and IL-1) and plateau levels of HMG1 were maintained for 16 to 32 hours. Patients with lethal sepsis had high serum HMG1 levels, which were not detected in normal healthy volunteers. Moreover, acute experimental administration of rHMG1 to test animals, whether alone or in combination with sub-lethal amounts of LPS, caused marked pathological responses and even death. More distributed dosing schedules of lower amounts of rHMG1 led to significant weight loss in treated animals. These results give evidence that HMG1 is a mediator of endotoxemia and particularly a late mediator, as opposed to known "early" mediators such as TNF and IL-1. These data further show the importance of serum HGM1 as a marker for the severity or potential lethality of sepsis and related conditions.

In addition, treatment with anti-HMG1 antibodies provided full protection from $LD_{100}$ doses of LPS in mice. HMG1 is inducible by TNF and IL-1β, and dose-dependently stimulates TNF release from huPBMCs. TNF is a marker of macrophage activation, so it is likely (without limitation as to implied mechanisms or being bound by theory) that HMG1 promotes downstream re-activation of cytokine cascades which, in turn, mediates late pathogenesis and lethality in sepsis and related conditions involving activation of pro-inflammatory cytokine responses. Thus, HMG1 likely occupies a central role in mediating the inflammatory response to infection and injury, and antagonists of HMG1 will be of therapeutic benefit in sepsis and related conditions of inflammatory cascade activation. The appearance of HMG1 in the inflammatory cytokine cascade is suitable to propagate later phases of the host response and contribute to toxicity and lethality. The predictive data provided herein support the therapeutic efficacy of HMG1 antagonists and provide evidence in support of the aforementioned theory regarding mechanism of action. The in vivo treatment data showed the efficacy of HMG1 antagonists in general, and anti-HMG1 antibodies in particular, for treating conditions mediated by the inflammatory cytokine cascade in general and particularly sepsis conditions, including, for example, septic shock, sepsis syndrome or other "sepsis-like" conditions mediated by inflammatory cytokines. Further, the independent pathogenicity and toxicity/lethality of HMG1 shows that HMG1 antagonists are particularly effective when co-administered with antagonists of "early" inflammatory mediators such as TNF, MIF, IL-1 and IL-6.

In summary, HMG1 is a cytokine mediator of inflammatory reactions because: 1) HMG1 is released from macrophages and pituicytes following stimulation with bacterial toxins or with pro-inflammatory cytokines (TNF or IL-1β), 2) HMG1 accumulates in serum of animals exposed to LPS and in patients with sepsis; and 3) HMG1-specific antibodies protect against mortality in a predictive lethal endotoxemia animal model of clinical sepsis and related conditions.

Pharmaceutical Composition and Method of Administration

The inventive pharmaceutical composition or inventive pharmaceutical combination can be administered to a patient either by itself (complex or combination) or in pharmaceutical compositions where it is mixed with suitable carriers and excipients. The inventive pharmaceutical composition or inventive pharmaceutical combination can be administered parenterally, such as by intravenous injection or infusion, intraperitoneal injection, subcutaneous injection, or intramuscular injection. The inventive pharmaceutical composition or inventive pharmaceutical combination can be administered orally or rectally through appropriate formulation with carriers and excipients to form tablets, pills, capsules, liquids, gels, syrups, slurries, suspensions and the like. The inventive pharmaceutical composition or inventive pharmaceutical combination can be administered topically, such as by skin patch, to achieve consistent systemic levels of active agent. The inventive pharmaceutical composition or inventive pharmaceutical combination can be formulated into topical creams, skin or mucosal patches, liquids or gels suitable for topical application to skin or mucosal membrane surfaces. The inventive pharmaceutical composition or inventive pharmaceutical combination can be administered by inhaler to the respiratory tract for local or systemic treatment.

The dosage of the inventive pharmaceutical composition or inventive pharmaceutical combination of the present invention can be determined by those skilled in the art from this disclosure. The pharmaceutical composition or inventive pharmaceutical combination will contain an effective dosage (depending upon the route of administration and pharmacokinetics of the active agent) of the inventive pharmaceutical composition or inventive pharmaceutical combination and suitable pharmaceutical carriers and excipients, which are suitable for the particular route of administration of the formulation (i.e., oral, parenteral, topical or by inhalation). The active agent is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active agent or combination in water-soluble form. Additionally, suspensions of the active agent may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the active agent or combination to allow for more concentrated solutions.

Pharmaceutical formulations for oral administration can be obtained by combining the active agent with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a disintegrating agent may be added, and a stabilizer may be added.

Antisense Oligomers

The present invention provides antisense oligomers having a sequence effective to inhibit or block the expression of the HMG1 gene or mRNA sequence. Anti sense technology, which uses specific-oligonucleotides to inhibit expression of target gene products, is developing as a therapeutic modality for human disease. Several selection criteria are available to contribute to the optimization of antisense oligonucleotide antagonists. For example, it is advisable to choose sequences with 50% or more GC content. Preferred sequences span the AUG initiation codon of the target protein, but sites in the coding region and 5' UTR may perform equally well. Such sequences are generally about 18–30 nucleotides long and chosen to overlap the ATG initiation codon from the HMG1 cDNA sequence to inhibit protein expression. Longer oligomers are often found to inhibit the target to a greater extent, indicating that a preferred length is about 25 mer for the first oligonucleotides chosen as antisense reagents. Typically, three oligonucleotide sequences are chosen with regard to these criteria, and compared for antagonist activity to control oligonucleotide sequences, such as "reverse" oligonucleotides or those in which about every fourth base of the antisense sequence is randomized. Therefore, a preferred sequence for making antisense oligomer sequences to HMG1 is a 25 mer sequence chosen to overlap the ATG initiation codon (underlined) from the HMG1 cDNA sequence:

[SEQ ID NO. 5]
GAGGAAAAATAACTAAACATGGGCAAAGGAGATCCTAAGAAG and such preferred antisense sequences are used to construct antisense oligonucleotide agents (and suitable controls) for an its vitro comparison as antagonists of HMG1. These in vitro data are predictive of human clinical utility using antisense agents of comparable design.

HMG1-Directed Antibodies

The antibodies disclosed herein may be polyclonal or monoclonal; may be from any of a number of human, non-human eukaryotic, cellular, fungal or bacterial sources; may be encoded by genomic or vector-borne coding sequences; and may be elicited against native or recombinant HMG1 or fragments thereof with or without the use of adjuvants, all according to a variety of methods and procedures well-known in the art for generating and producing antibodies. Generally, neutralizing antibodies against HMG1 (i.e., those that inhibit biological activities of HMG1 particularly with regard to its pro-inflammatory cytokine-like role) are preferred for therapeutic applications while non-neutralizing antibodies may be as suitable for diagnostic applications. Examples of such useful antibodies include but are not limited to polyclonal, monoclonal, chimeric, single-chain, and various human or humanized types of antibodies, as well as various fragments thereof such as Fab fragments and fragments produced from specialized expression systems.

Diagnostic Assay

The diagnostic assay provided here uses anti-HMG1 antibodies that can be either polycolonal or monoclonal or both. The diagnostic procedure can utilize standard antibody-based techniques for measuring concentrations of the gene product of HMG1 genes in a biological fluid. Preferred standard diagnostic procedures are ELISA assays and Western techniques.

EXAMPLE 1

Identification of HMG1 as a "late" Mediator of Endotoxemia

This example provides the results of an experiment to identify and isolate later released macrophage-derived factors that play a role in sepsis and in related conditions typified by inflammatory cytokine activity. The experiment reported in this example examined murine macrophage RAW 264.7 cell-conditioned media after stimulation of the cultures with TNF. Murine macrophage RAW 264.7 cells were obtained from American Type Culture Collections (ATCC, Rockville, Md. USA), and proliferated in culture under DMEM supplemented with 10% fetal bovine serum and 1% glutamine. When confluency reached 70–80%, the medium was replaced by serum-free OPTI-MEM I medium and cultures were stimulated with pro-inflammatory cytokines (e.g., TNFα or IL-1) or bacterial endotoxin (LPS).

The proteins released from the above stimulated macrophage cultures were surveyed. Specifically, at different time points, cells and cell-conditioned media were separately collected by centrifugation (3000 rpm, 10 minutes). Proteins in the conditioned mediam were concentrated by ultrafiltration over Amicon membranes with Mr cutoff of 10 kDa (Amicon Inc., Beverly, Mass., USA), subsequently fractionated by SDS-PAGE, and stained with Coomassie blue (1.25% Coomassie Blue R250 in 30% methanol/10% acetic acid). After destaining with 30% methanol/7% acetic acid, protein(s) of interest (i.e., those that preferentially accumulated in conditioned media of stimulated cultures) was isolated by excision from the SDS-PAGE gel, and subjected to N-terminal sequencing analysis (Commonwealth Biotechnologies, Inc., Richmond, Va., USA).

Comparison of SDS-PAGE gel analysis of profiles of proteins accumulated in control (without TNFα stimulation) versus TNF-stimulated RAW 264.7 cells revealed a strongly inducible 30 kDa protein whose concentration in the cell-conditioned medium was significantly increased after stimulation for 16 hours. Amino acid sequence analysis of this isolated protein revealed its N-terminal sequence as Gly-Lys-Gly-Asp-Pro-Lys-Lys-Pro-Arg-Gly-Lys-Met-Ser-Ser [SEQ ID NO. 1]. A review of relevant gene databases found a 100% identity to the N-terminal amino acid sequence of HMG1.

These data identified HMG1 as a "late-appearing" product of LPS-stimulated macrophage cultures, and therefore as a candidate pro-inflammatory mediator. This activity was confirmed by administration of recombinantly produced HMG1 and/or of anti-HMG1 antibodies in cellular and animal model systems that are predictive of human clinical conditions.

EXAMPLE 2

Cellular Sources of HMG1

This example shows which cell sources are capable of releasing HMG1 in response to TNF, IL-1 and/or LPS. Cells studied include $GH_3$ pituicytes, murine macrophage RAW 264.7 cells, human primary peripheral blood mononuclear cells (huPBMCs), human primary T cells, rat adrenal PC-12 cells, and rat primary kidney cells (Table 1). The rat pituitary $GH_3$ cell line was obtained from American Type Culture Collection (ATCC, Rockville, Md., USA), and cultured in DEME supplemented with 10% fetal bovine serum and 1% glutamine. Human PBMCs and T cells were freshly isolated from whole blood of healthy donors and cultured in RPMI 1640 supplemented with 10% human serum as previously described (Zhang et al., *J Exp. Med*. 185:1759–1768, 1997). When confluency reached 70–80%, the medium was replaced by serum-free OPTI-MEM I medium and cultures stimulated with proinflammatory cytokines (e.g., TNFα or IL-1) or bacterial endotoxin (LPS).

Although human T cell, rat adrenal (PC-12) cells, and rat primary kidney cells contained cell-associated HMG1 as demonstrated by Western blotting analysis of whole cell lysates using HMG1-specific antibodies (see Example 4 below), HMG1 did not significantly accumulate in the medium of these cultures after stimulation with either TNF, IL-1β, or LPS (Table 1).

TABLE 1

Induced release of HMG1 from various types of cells.

| Cell Type | Stimulus | | |
|---|---|---|---|
| | TNF | IL-1β | LPS |
| Murine RAW 264.7 cells | Yes | Yes | Yes |
| Human PBMCs | Yes | Yes | Yes |
| Human primary T cells | No | No | No |
| Rat adrenal PC-12 cells | No | No | No |
| Rat pituitary $GH_3$ cells | Yes | Yes | No |
| Rat primary kidney cells | No | No | No |

Note:
PBMCs, peripheral blood mononuclear cells.

TNF, IL-1β (minimal effective concentration=5 ng/ml for each) and bacterial endotoxin (LPS, minimal effective concentration=10 ng/ml) induced the release of HMG1 from human PBMCs in a time- and dose-dependent manner (Table 1). IFN-γ alone (0–200 U/ml) did not induce HMG1 release from any of the above cells, but when added in combination either with TNF or IL-1β, IFN-γ dose-dependently enhanced HMG1 release from macrophages, with a maximal 3-fold enhancement by IFN-γ at a concentration of 100 U/ml. The release of HMG 1 was not due to cell death, because cell viability was unaffected by TNF, IL-1β, or LPS, as judged by trypan blue exclusion (90–92±5% viable for control vs. 88–95±4% in the presence of 100 ng/ml TNF, IL-1β or LPS). The amount of HMG1 released by pituicytes and macrophages inversely correlated with the intracellular concentration of HMG1, as determined by Western blotting analysis, indicating that the released material is, in part derived from pre-formed cell-associated HMG1 protein.

Figure 5:
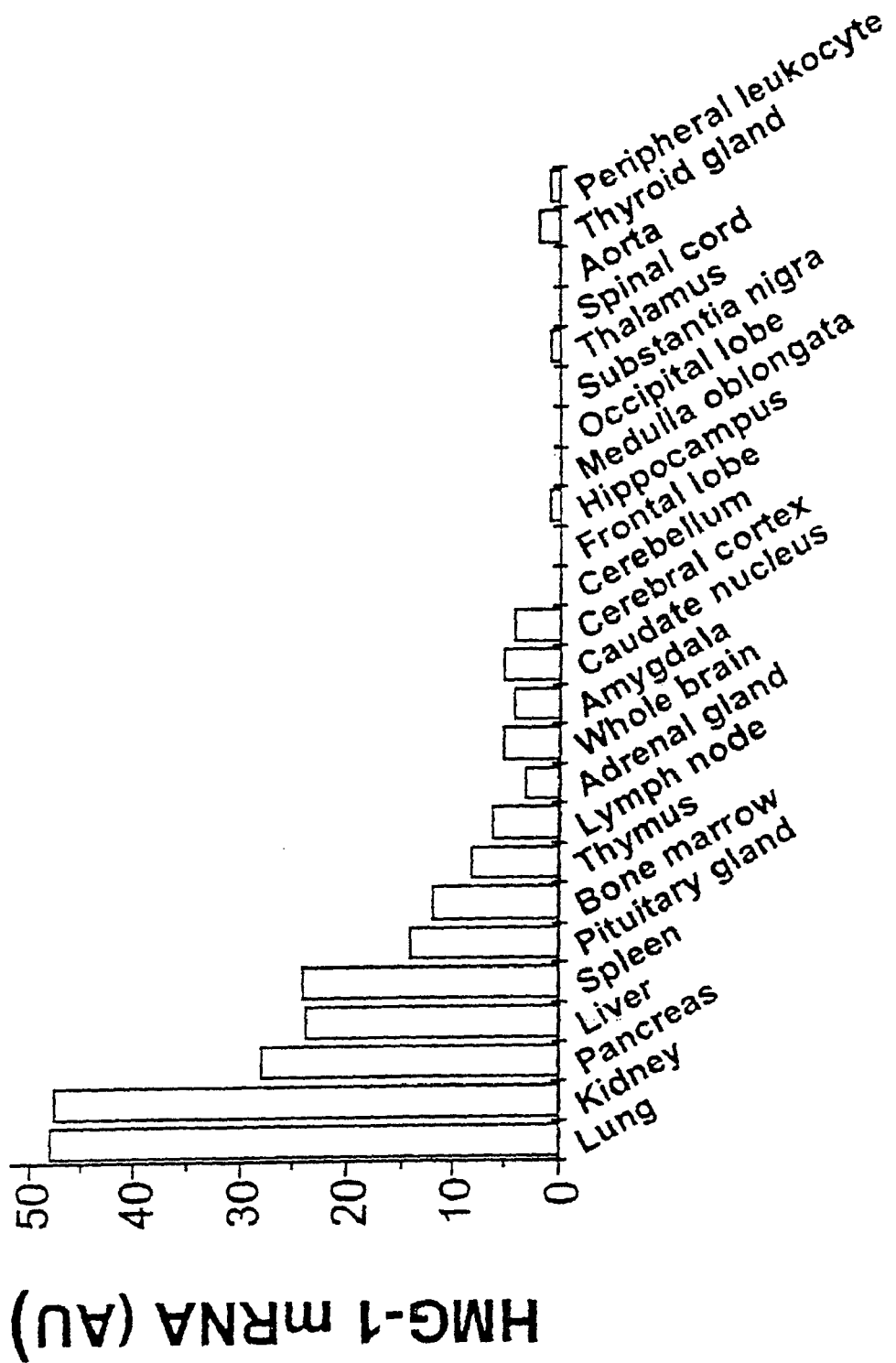
FIG. 5 shows the tissue distribution of HMG1 mRNA. Human RNA master blots containing poly(A)$^+$ RNA of various tissues (Clontech, Palo Alto, Calif. USA) were hybridized with a 0.6 kb digoxigenin-11-dUTP-labeled HMG1 cDNA probe synthesized by PCR using recombinant plasmid containing the HMG1 cDNA insert, all in accordance with methods well-known in the art. Briefly, hybridization was performed in a hybridization buffer (5×SSC/2% blocking reagent/0.1% SDS/50% formamide, Boehringer Mannheim, Indianapolis, Ind.) with a probe concentration of 10 ng/ml for 16 hours at 65° C. After hybridization, the filter was subjected to two washes of 0.5×SSC/0.1% SDS for 5 minutes, and two washes of 0.2×SSC/0.1% SDS for 10 minutes at room temperature. Signal was detected using anti-digoxigenin antibodies conjugated to phosphotase and detection reagents 4-nitrobluetetrazolium chloride (NBT) and 5-cromo-4-chloro-3-indolyl-phosphate (BCIP) (Boehringer-Manuheim) according to standard methods. The blots were scanned with a silver image scanner (Silverscanner II, Lacie Limited, Beaverton, Oreg.), and relative optical density (in arbitrary units, AU) was quantified using NIH 1.59 image software. Note that highest levels were observed in macrophage-rich tissues.

Potential sources of circulating HMG1 in vivo were assessed by hybridization of an HMG1-specific probe to mRNA prepared from various normal human tissues (blot substrate available from commercial sources), with the results summarized in FIG. 5. Several macrophage-rich tissues (lung, liver, kidney, pancreas and spleen) exhibited the most abundant HMG1 mRNA expression; less was observed in pituitary, bone marrow, thymus, lymph node and adrenal gland. In addition to providing information as to the relative tissue distribution of HMG1 expression, this study shows the practicality and utility of assaying for HMG1-specific nucleic acid sequences in tissue samples.

EXAMPLE 3

Recombinant HMG1 Administration, in vitro and in vivo

This example details procedures to produce HMG1 by well-known recombinant DNA technologies. The HMG1 open reading frame was amplified by PCR and subcloned into an expression vector (pCAL-n). Briefly, the 648-bp open reading frame of HMG1 cDNA was PCR amplified (94° C. 1', 56° C. 2', 72° C. 45", 30 cycles) from 5 ng Rat Brain Quick-Clone cDNA (Catalog #7150-1, Clontech, Palo Alto, Calif., USA) using primers containing the following sequences, 5'-CCC GCG GAT CCA TCG AGG GAA GGA TGG GCA AAG GAG ATC CTA-3'[SEQ ID NO. 2], and 5'-CCC GCA AGC TTA TTC ATC ATC ATC ATC TTC T-3'[SEQ ID NO. 3]. The 680 bp PCR product (4 μg) was digested with Bam HI and Hind III, and cloned into the Bam HI/Hind III cloning sites of the pCAL-n vector (Stratagene, La Jolla, Calif., USA). The recombinant plasmid was transformed into *E. coli* BL21(DE3)pLysS (Novagen, Madison, Wis., USA), and positive clones were screened and confirmed by DNA sequencing on both strands using a Taq DyeDeoxy terminator cycle sequencing kit on the ABI 373A automated fluorescent sequencer (Applied Biosystems, Foster City, Calif., USA).

To express recombinant HMG1, positive clones were cultured at 37° C. with vigorous shaking (250 rpm) until $OD_{600}$ reached 0.6, when IPTG (1 mM) was added. Twelve hours after IPTG induction, bacterial cells were harvested by centrifugation (6500 rpm, 15 minutes), and lysed by freeze-thaw cycles. The water-soluble fraction was collected after centrifugation (30 minutes, 12,000 rpm), and recombinant HMG1 was purified on a calmodulin-binding resin column as instructed by the manufacturer (Stratagene). Bacterial endotoxin was removed from the recombinant HMG1 by using Detoxi-Gel endotoxin-removing gel (Pierce, Rockford, Ill. USA, Cat. #20344), and residual LPS content was determined by the Limulus Amebocyte Lysate Test (LAL, test, Cat. #50-648U, QCL-1000 Chromogenic LAL, Bio-Whittaker, Inc., Walkersville, Md., USA). Purified recombinant HMG1 was added to cultures of human peripheral blood mononuclear cells (HuPBMCs), and supernatants assayed for TNF by ELISA four hours after stimulation. The LPS-neutralizing agent polymyxin B (10 μg/ml) was added concurrently with recombinant HMG1 to eliminate the effect of any contaminating LPS on TNF release. Additionally, recombinantly derived HMG1 was administered to test animals, with or without the additional endotoxemic challenge of exogenous LPS, to study the pathogenic potential of high levels of HMG1 in vivo (see FIGS. 2B and 2C). In some experiments, serum samples were secured from HMG1-treated animals to be assayed for TNF as detailed herein (see FIG. 1B).

The above procedure provides recombinant HMG1 as a fusion peptide comprising a 3.0 kDa calmodulin-binding domain and a thrombin cleavage site as an amino terminal extension in register with the HMG1 peptide sequence. In some experiments, the fusion tag was removed from an aliquot of the recombinant protein and the bioactivity of the full fusion protein was compared to the cleaved HMG1 peptide; no significant difference in bioactivity was noted and additional experiments (especially those requiring administration of recombinantly produced HMG1 to animals) typically were conducted with the (uncleaved) fusion protein.

Figure 3A:
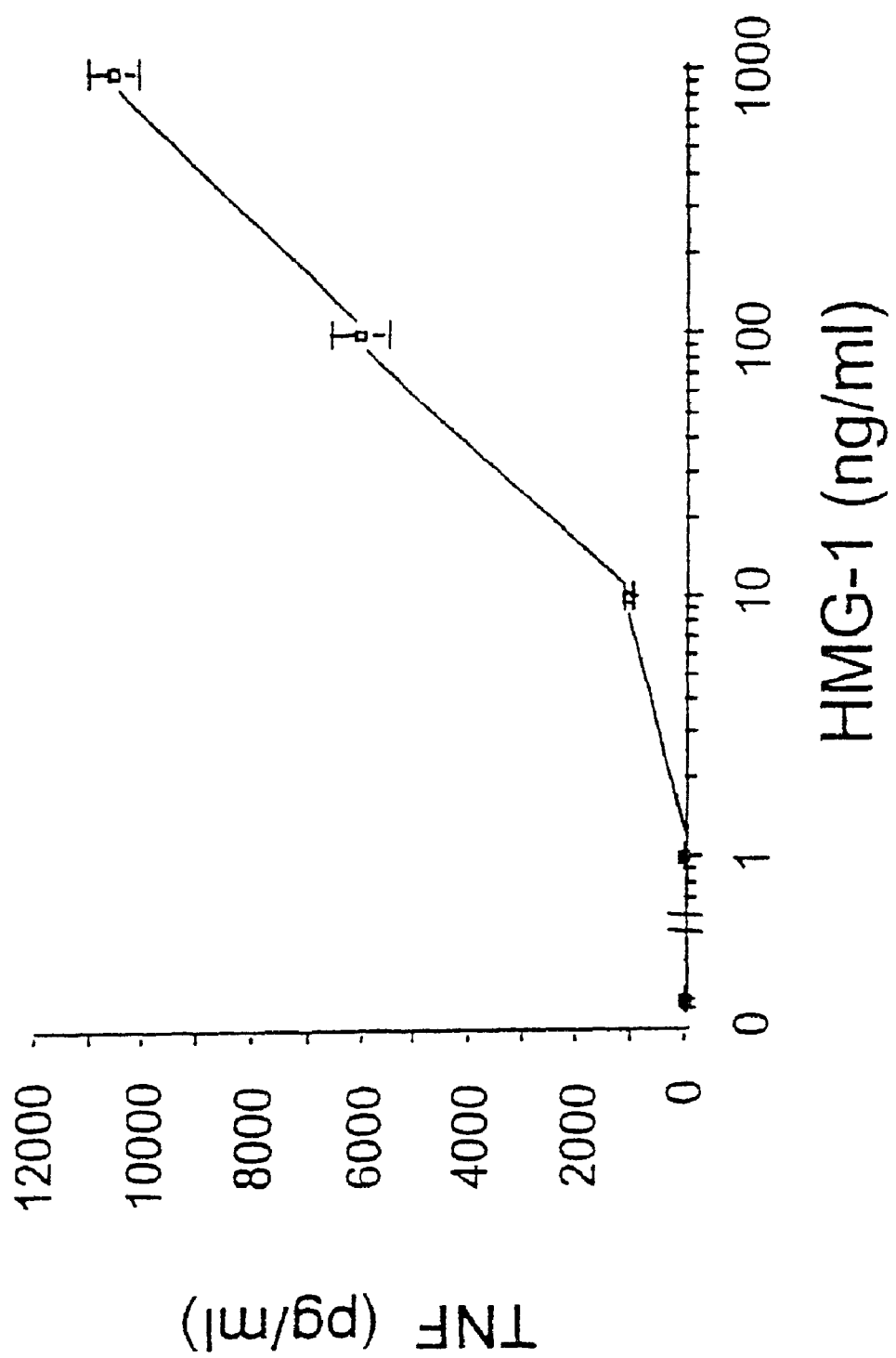
FIG. 3A shows that HMG1 induces TNF release from huPBMCs in dose-dependent fashion. Freshly isolated huPBMC cultures were stimulated with purified recombinant HMG1 protein at the indicated doses, and culture media were sampled four hours later to be assayed for TNF according to known immunologic methods (ELISA).
Figure 3B:
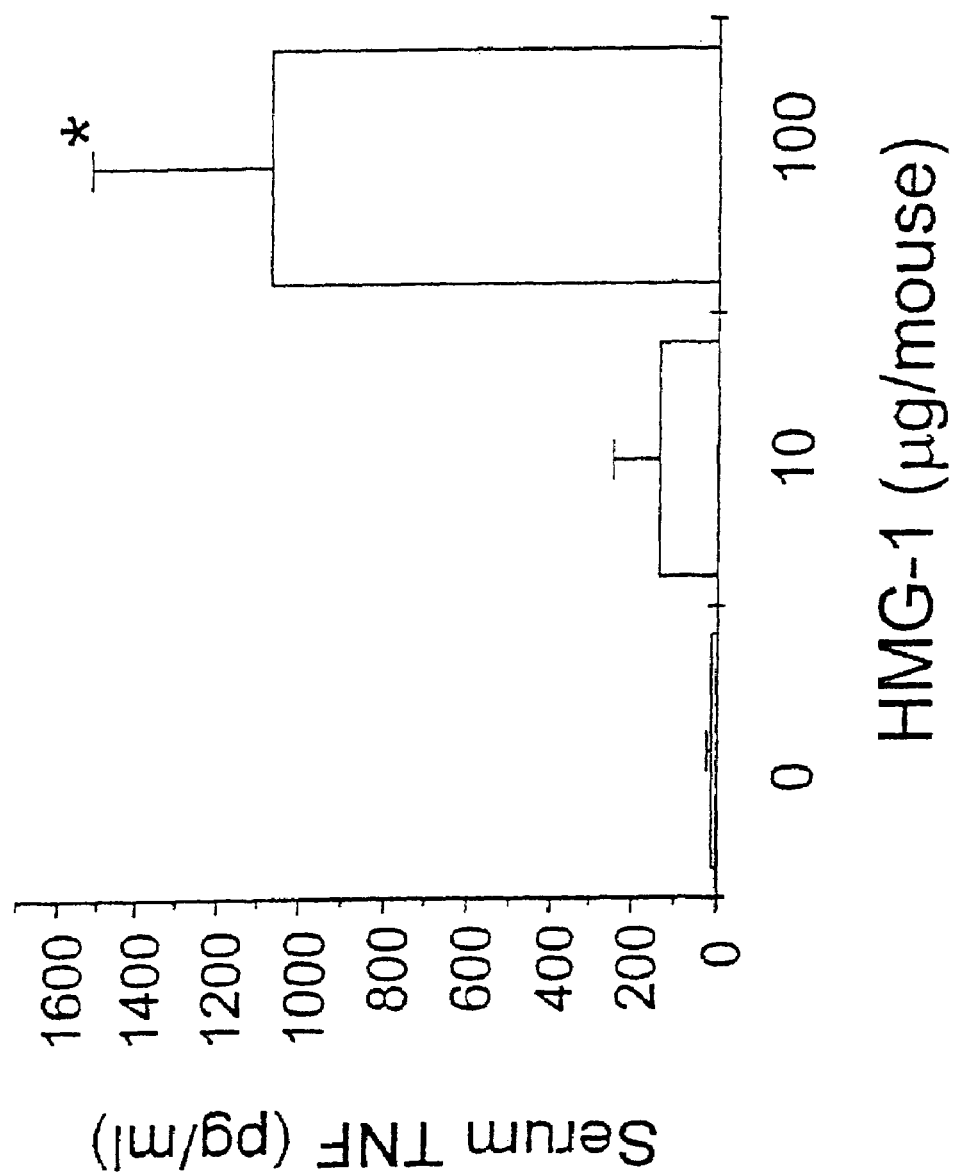
FIG. 3B shows that administration of HMG1 induced accumulation of TNF in serum of treated mice. Balb/C mice (20–23 g) were treated intraperitoneally with purified recombinant HMG1 at the indicated doses and blood samples were taken two hours later for assay of TNF by an L929 bioassay and (TNF levels expressed as mean ±S.E.M., N=3).

As demonstrated in FIGS. 3A and 3B, in vitro or in vivo administration of recombinantly derived HMG1 induced a brisk TNF response, confirming the identification of HMG1 as a late-appearing LPS-induced macrophage-derived endogenous mediator with pro-inflammatory activity.

EXAMPLE 4

Anti-HMG1 Antibodies and Immunodetection

This example provides the results of experiments to generate and use polyclonal antibodies against HMG1. Briefly, polyclonal antibodies against an oligopeptide corresponding to the N-terminal amino acid sequence of HMG1, or against purified recombinant HMG1, were generated in rabbits according to standard procedures well known in the art. Briefly, eight copies of an oligopeptide with the sequence GKGDPKKPRGKMSSC [SEQ ED NO. 4] were anchored to radially branching lysine dendrites (small immunogenically inert core). These large macromolecules were injected three times both subcutaneously and intradermally (0.5–1.0 mg per injection) into rabbits at week 1, 2, and 4 after pre-bleed at Day 0. Two weeks after the last immunization, rabbits were bled and boosted intramuscularly with 1.0 mg of antigen, followed by a second bleeding two weeks later. Alternatively, to produce polyclonal antibodies against recombinant HMG1, rabbits were immunized with recombinant HMG1 fusion peptide (100 μg per injection) following a similar protocol. Monoclonal antibodies reactive against HMG1 (i.e., that bind, and in some cases, neutralize or antagonize the biological activity of HMG1) are conveniently prepared according to methods well known in the art using the HMG1 antigens described herein or other HMG1 peptide fragments as immunogens. Such monoclonal antibodies, and/or the hybridomas that produce them, are useful to produce various "humanized" antibodies reactive against HMG1 (all according to methods known in the art), which humanized antibodies; are useful as taught herein.

HMG1-specific antibodies were used to measure by Western blotting analysis the inducible release of HMG1 from RAW 264.7 cells after treatment with TNF or LPS (FIG. 1). Briefly, proteins were fractionated by SDS-PAGE on a 4–20% gradient gel, transferred to a PVDF membrane, and blotted with rabbit antiserum raised against either the N-terminal synthetic HMG1 antigen or against recombinant HMG1. The signal was detected using a ECL kit as instructed by the manufacturer (Amersham Life Science Inc., Arlington Heights, Ill., USA), and levels of HMG1 were determined by measuring optical intensity of bands on Western blots digitized for analysis using NIH 1.59 image software, with reference to a standard curve of purified recombinant HMG1.

Figure 1B:
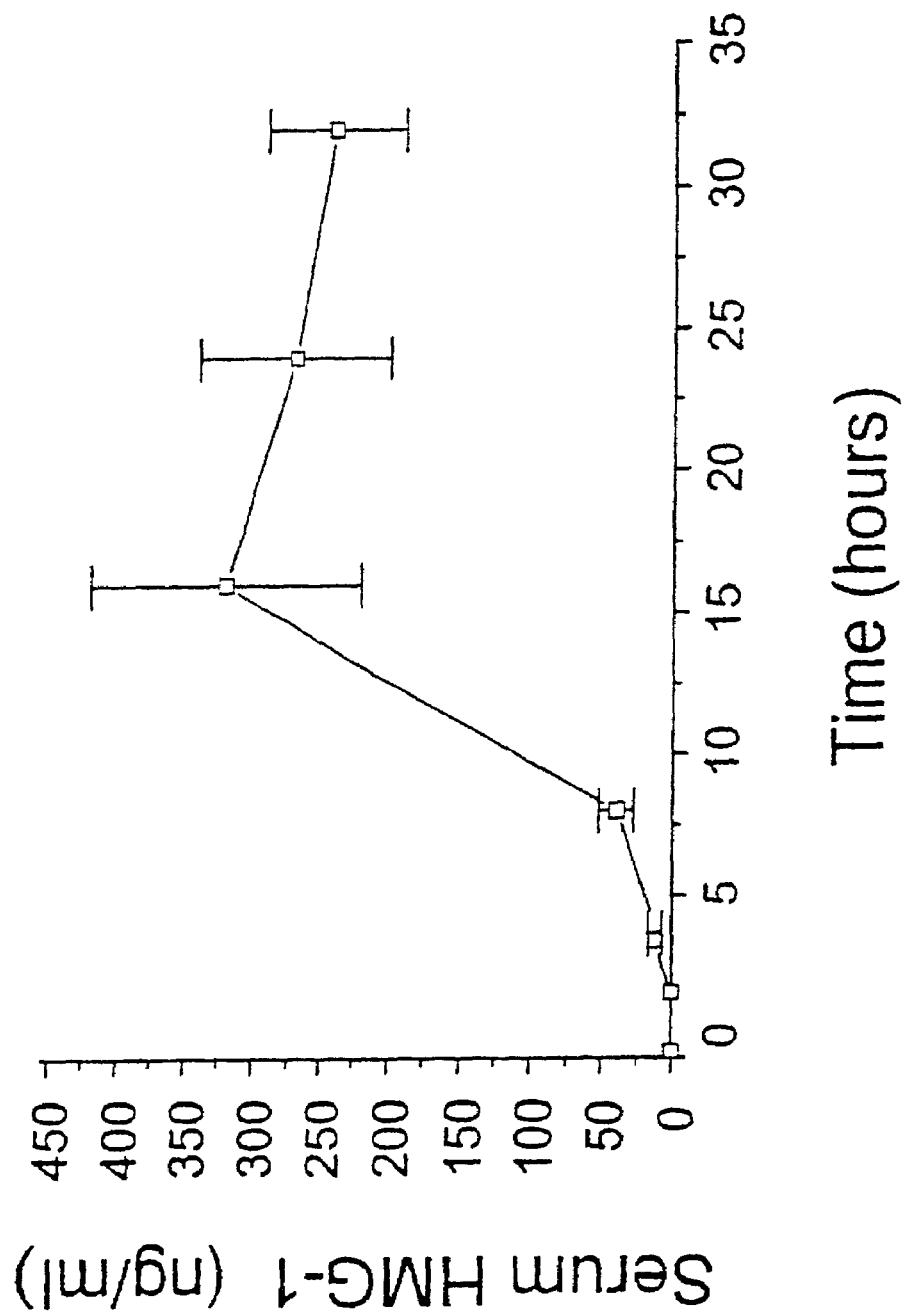
FIG. 1B shows accumulation of HMG1 in serum of LPS-treated mice. Serum from Balb/C mice was collected at various time points after LPS administration, and assayed for HMG1 by Western blotting using antibodies raised against recombinant HMG1.

No HMG1 protein was detected in RAW 264.7 cells-conditioned medium in the absence, of TNF or LPS treatment, but HMG1 accumulated in conditioned medium to high levels after such stimulation, reaching a plateau at 8–28 hours after stimulation (FIG. 1A). In summary, the data presented in Examples 1, 3 and in FIG. 1A show that the release of HMG1 from macrophages is stimulus-specific and time- and dose-dependent, with maximal accumulation observed within 8 hours after stimulation with TNF at concentrations as low as 5 ng/ml. It is well appreciated that sepsis, septic shock and related conditions may occur in humans in response to stimuli that differ qualitatively or quantitatively from the single large, lethal LPS bolus used in this predictive models. Nevertheless, experimental endotoxemia has been a valuable and predictive model system by which to identify critical components of the inflammatory cytokine cascade and by which to identify specific antagonists with predicted clinical utility. In this regard, HMG1 antagonists are perhaps more therapeutically attractive than TNF antagonists in view of the later appearance of HMG1 versus TNF in the response to endotoxin.

EXAMPLE 5

Detection of HMG1 in in vivo Animal Models

This example illustrates an in vivo experiment in rodents measuring serum HMG1 levels after administration of a sublethal dose of LPS ($LD_{50}$). Mice or rats were treated with LPS, and sera were collected at different time points, and assayed for levels of HMG1 by Western blotting analysis. The serum concentrations of HMG1 were estimated by measuring the optical band intensity with reference to a standard curve of purified HMG1. Serum levels increased significantly by 16 hours after LPS, and remained high for at least 32 hours (FIG. 1B), and were not detectable in vehicle-treated control animals. These data show that HMG1 represents a particularly attractive target for diagnosis of, and pharmaceutical intervention against, sepsis and related disorders of cytokine toxicity because HMG1 is a late-appearing mediator in the inflammatory cytokine cascade.

EXAMPLE 6

Benefits of Protection Against HMG1

This example provides the results of a predictive in vivo assay to measure therapeutic activity of antagonists of HMG1 in relation to treatment of sepsis and related conditions of cytokine-mediated toxicity. In this example, the HMG1 antagonist was an anti-HMG1 antibody preparation. Controls treated with pre-immune serum developed lethargy, piloerection, diarrhea, and succumbed to death within 48 hours. These clinical signs of endotoxemia were significantly prevented by administration of anti-HMG1 antibodies. Male Balb/C mice (6–7 weeks, 20–23 grams) were randomly grouped (10 animals per group) and pre-treated either with control (pre-immune) or anti-HMG1 serum (as made in Example 4) 30 minutes before administration (intraperitoneally) of a lethal dose of LPS (50 mg/kg in 1×PBS). Other experimental groups received additional doses of anti-HMG1 serum at +12 or, +12, and +36 hours after LPS administration. Animals were observed for appearance and survival for at least two weeks.

Polyclonal antibodies against recombinant HMG1 were generated in rabbits, and antiserum was assayed for specificity and titer by ELISA and Western blotting procedures. The polyclonal antiserum immunospecifically recognized (bound to) recombinant HMG1 in Western blot analysis, for instance, and discriminated rHMG1 from other proteins in both crude bacterial lysates and as a purified protein that had been diluted into mouse serum. Using chemiluminescence-amplified detection methods in Western blotting analysis, polyclonal anti-HMG1 antiserum at dilutions up to 1:1000 was useful to detect as little as 50 pg rHMG1 protein. Administration of anti-HMG1 antiserum in the indicated (FIG. 2A) amounts at −0.5 (if one dose), −0.5 and 12 (if two doses), or −0.5, 12 and 36 (if three doses) hours relative to LPS challenge (at time 0) was protective against LPS-induced lethality, and repeated dosing schedules provided better protection.

Figure 2A:
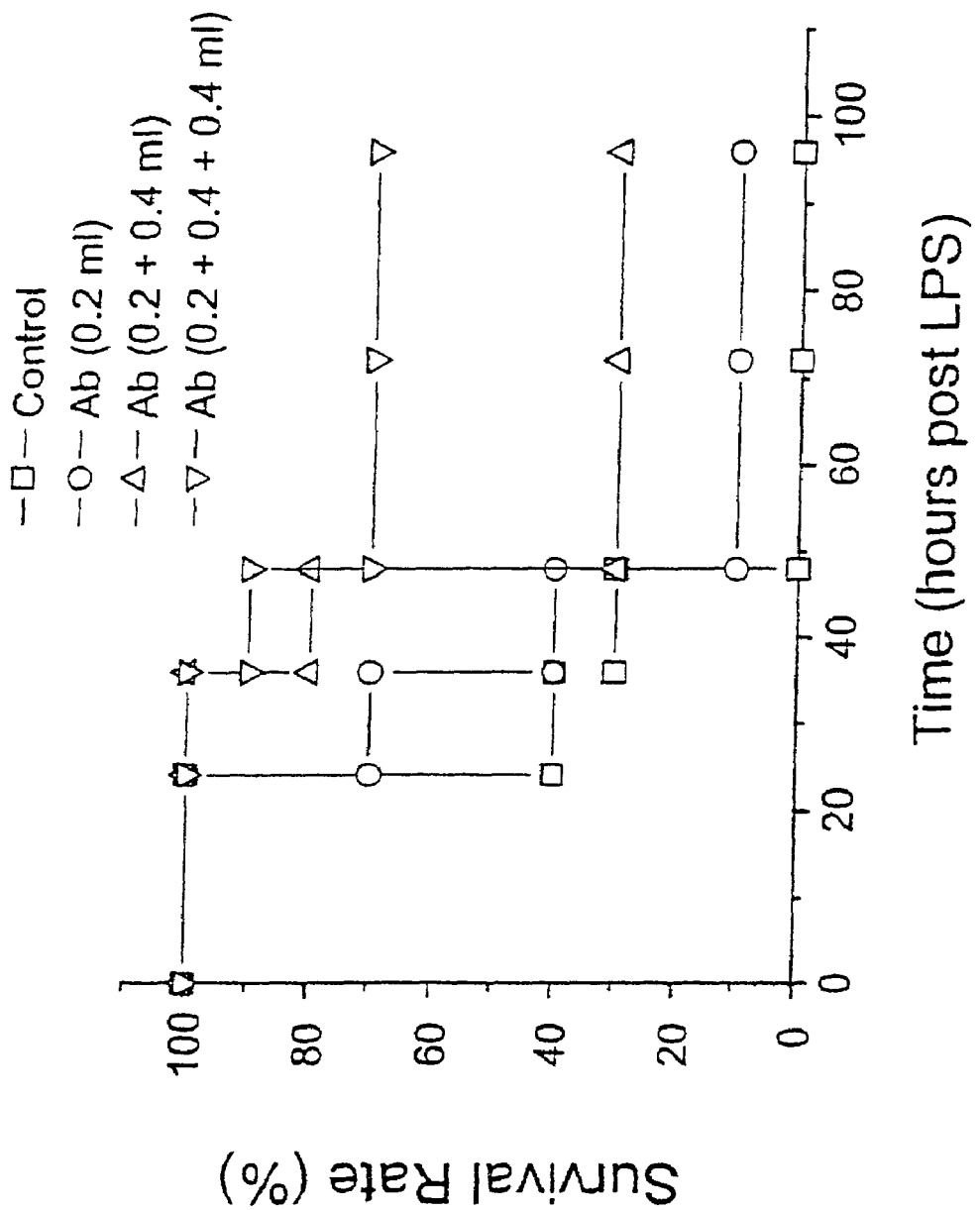
FIG. 2A shows the protective effect of anti-HMG1 antibodies against LPS lethality, tested in mice. Administration of anti-HMG1 antiserum in the indicated amounts at –0.5 (if one dose), –0.5 and 12 (if two doses), or –0.5, 12 and 36 (if three doses) hours relative to LPS challenge (at time 0) was protective against LPS-induced lethality, and repeated dosing schedules provided better protection.
Figure 2B:
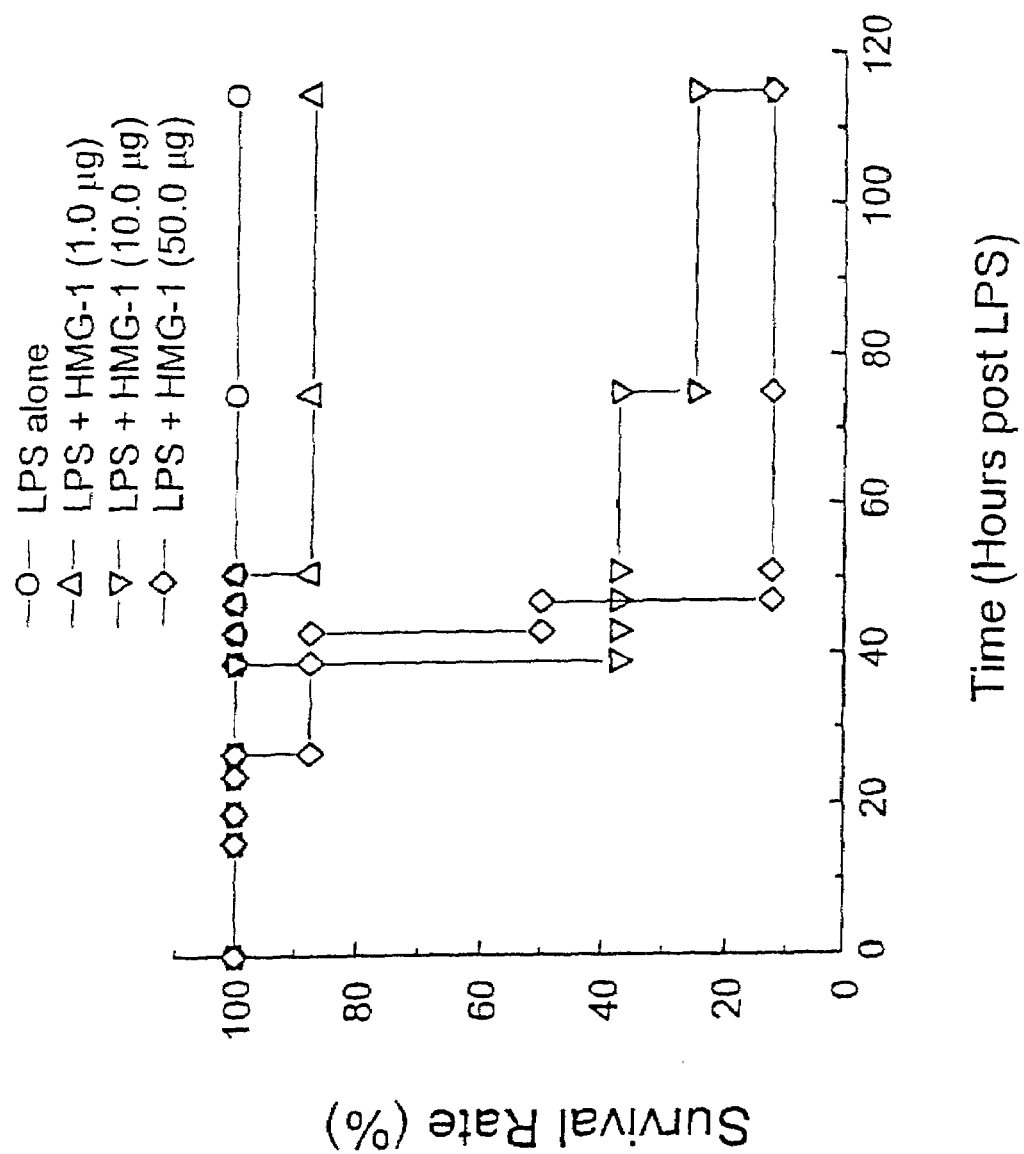
FIG. 2B illustrates that rHMG1 caused dose-dependent lethality in endotoxic mice. Male Balb/C mice (20–23 grams) were randomized in groups of ten to receive LPS (3.15 mg/kg; a non-lethal dose) alone or in combination with purified recombinant HMG1 protein. Administration of HMG1 at the indicated doses 2, 16, 28 and 40 hours after LPS challenge significantly increased the lethality of the underlying endotoxemia.
Figure 2C:
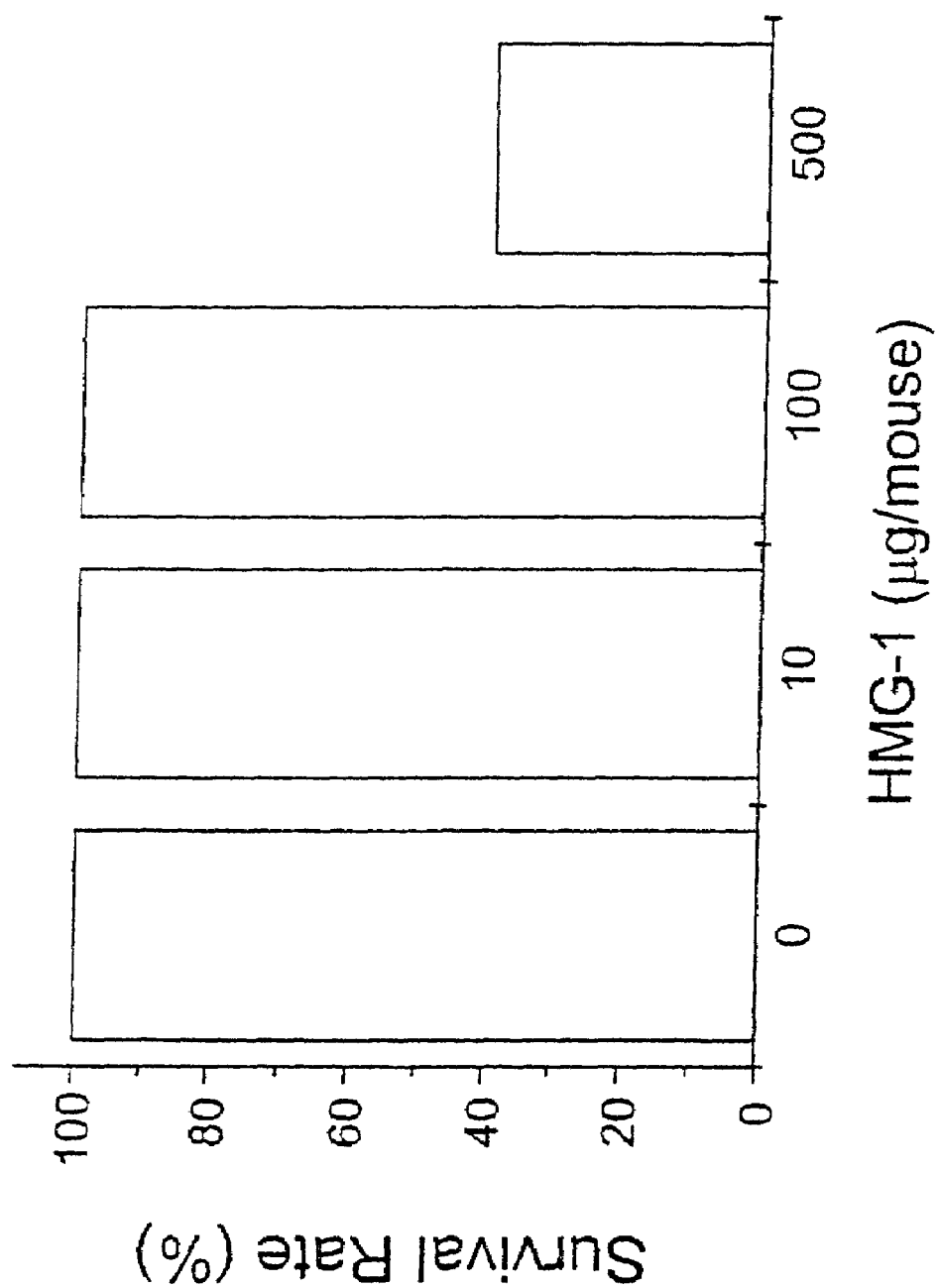
FIG. 2C illustrates independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 μg/mouse died within 24 hours of rHMG1 challenge, indicating a single dose $LD_{50}$ of less than 500 μg/mouse.

FIG. 2B illustrates that rHMG1 causes dose-dependent lethality in endotoxic mice. Male Balb/C mice (20–23 grams) were randomized in groups often to receive LPS (3.15 mg/kg; a non-lethal dose) alone or in combination with purified recombinant HMG1 protein. Administration of HMG1 at the indicated doses 2, 16, 28 and 40 hours after LPS challenge significantly increased the lethality of the underlying endotoxemia FIG. 2C illustrates the independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 μg/mouse died within 24 hours of rHMG1 challenge, indicating a single dose $LD_{50}$, of less than 500 μg/mouse.

The protection conferred by anti-HMG1 antibodies was specific, because administration of pre-immune serum, which showed no immunospecific reactivity to HMG1 on Western blots, did not spare subjects from LPS-mediated mortality (FIG. 2A). Moreover, HMG1-specific antibodies did not cross-react with other macrophage-derived cytokines (e.g. IL-1 and TNF), eliminating the possibility that antibodies conferred protection by binding and thereby neutralizing these mediators. Protection against sepsis, sepsis associated pathogenesis and sepsis-related diseases involving activation of pro-inflammatory cytokine cascades may be improved by combination therapy targeted against more than one component of the cytokine cascade. Antagonists of HMG1 in this regard can be combined with specific antagonists of TNF, IL-1, MIF and other inflammatory mediators, or with more broadly active antagonists of inflammatory responses that inhibit multiple components of the inflammatory cascade (e.g., aspirin, NSAIDS, anti-inflammatory steroids, etc.), to provide even more effective therapeutic modalities. Protection against LPS toxicity was antibody dose-related, and more frequent dosing with higher amounts of antibody reduced mortality by up to 70% (FIG. 2A). Mice were observed for at least 2 weeks in all experiments, and no late mortality occurred, indicating that anti-HMG1 antibody treatment confers lasting protection against LPS lethality, and does not merely delay the time of death.

EXAMPLE 7

HMG1 in Human Disease

This example provides data that establish an association between HMG1 and human sepsis, and thereby support an indication for using HMG1 antagonists generally and anti-HMG1 antibodies in particular in human sepsis and related conditions of cytokine toxicity. Serum HMG1 levels in normal healthy individuals and critically ill patients were measured using the polyclonal antibodies generated as in Example 4 in a Western blot format with reference to a standard curve of rHMG1. HMG1 was not detectable in normal controls, but accumulated to high levels in critically patients with sepsis (Table 2).

TABLE 2

Serum appearance of HMG1 in sepsis patients.

| Patient (#) | Age (year) | HMG1 (ng/ml) | Diagnosis | Outcome |
|---|---|---|---|---|
| 1 | 27 | <d.l. | Normal | Healthy |
| 2 | 34 | <d.l. | Normal | Healthy |
| 3 | 35 | <d.l. | Normal | Healthy |
| 4 | 36 | <d.l. | Normal | Healthy |
| 5 | 61 | <d.l. | Normal | Healthy |
| 6 | 31 | <d.l. | Normal | Healthy |
| 7 | 55 | 10 | Sepsis, anastomotic leak | Recovered |
| 8 | 70 | 7–20 | Sepsis, colonic perforation | Recovered |
| 9 | 44 | 10–60 | Sepsis, MOF, spinal reconstruction | Died |
| 10 | 60 | >120 | Sepsis, MOF, perforated gastric ulcer | Died |
| 11 | 47 | >120 | Sepsis, MOF, pneumonia | Died |

Note:
<d.l.—below detection limit;
MOF—Multiple Organ Failure.

These data show that elevated serum HMG1 levels are observed in patients with sepsis, and the highest levels of serum HMG1 are observed in lethal cases (Table 2). These data further indicate the therapeutic importance of HMG1 antagonists in sepsis and also provide evidence for the diagnostic utility of an assay for sepsis and severity (i.e., potential lethality) of sepsis by measuring serum concentrations of HMG1. This diagnostic assay is also useful for diagnosing the severity of allied conditions involving activation of the inflammatory cytokine cascade.

Figure 6:
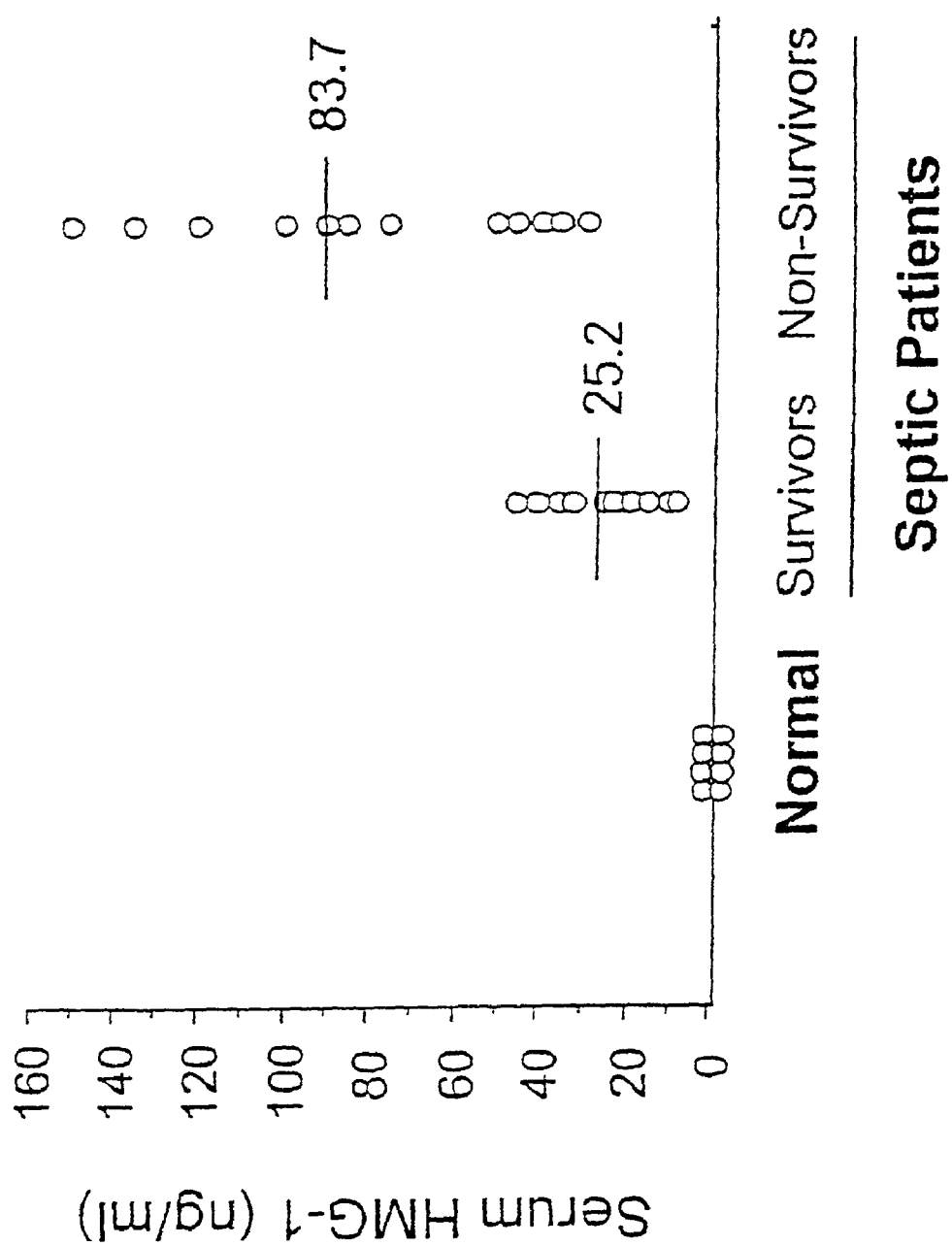
FIG. 6 shows, in comparison to a group of normal control subjects, increased human serum HMG1 levels as detected in hospitalized human subjects with sepsis, wherein the septic patients have been further categorized as to whether the patient died or survived.

Additional subjects were screened for serum HMG1 levels in association with lethal versus non-lethal sepsis, with results (cumulative with Table 2) as described in FIG. 6. The data summarized in FIG. 6 represent serum samples obtained from eight healthy subjects and twenty-five septic patients infected with Gram positive [*Bacillus fragilis* (1 patient), *Enterococcus facecalis* (1 patient), *Streptococcus pneumonia* (4 patients), *Listeria monocytogenes* (1 patient), or *Staphylococcus aureus* (2 patients)], Gram negative [*Escherichia coli* (7 patients), *Klebsiella pneumonia* (1 patient), *Acinetobacter calcoaceticus* (1 patient), *Pseudomonas aeruginosa* (1 patient), *Fusobacterium nucleatum* (1 patient), *Citrobacter freundii* (1 patient)], or unidentified pathogens (5 patients). Serum was fractionated by SDS-PAGE gel electrophoresis, and HMG1 levels were determined by Western blotting analysis with reference to standard curves of purified rHMG1 diluted in normal human serum. The detection limit by Western blotting analysis is 50 pg. Note that HMG1 is not detectable in normal controls, but significantly increased in septic patients. The average level of HMG1 in serum of non-surviving septic patients (N=13 patients, mean HMG1 level=83.7±22.3 ng/ml) is significantly higher than in survivors (N=12, mean HMG1 level=25.2±15.1 ng/ml, P<0.05). These data provide direct evidence of the utility of screening tissue (including, without limitation blood or serum) samples for HMG1 sequences (protein or nucleic acid) as a diagnostic and prognostic indicator of the presence of sepsis and related disorders of cytokine activation and of the severity and likely clinical course of such diseases and conditions.

EXAMPLE 8

HMG1 Induces Pro-Inflammatory Mediators and Weight Loss

The present results provide evidence that HMG1 is a late released mediator element of the inflammatory cytokine cascade. Addition of recombinant HMG1 to primary human peripheral blood mononuclear cells led to the dose-dependent induction of TNF within four hours after stimulation (FIG. 3A). This stimulation by recombinant HMG1 of TNF release by HuPBMCs was not due to LPS contamination because: i) purified recombinant HMG1 was not contaminated by LPS as judged by an LAL endotoxin assay; ii) addition of the LPS-neutralizing agent polymyxin B did not affect HMG1-induced TNF release; and iii) proteolytic cleavage of recombinant HMG1 preparations with trypsin completely abolished the TNF release activity for the PBMC cultures. HMG1 stimulation also induced macrophages to release nitric oxide (NO).

To confirm that HMG1 induced serum TNF release it vivo, purified recombinant HMG1 was administered intraperitoneally to Balb/C mice, and blood samples were collected to be assayed for TNF by the L929 assay. As shown in FIG. 3B, TNF was not detectable in serum of control animals, but was significantly increased two hours after administration of recombinant HMG1 protein.

Figure 4:
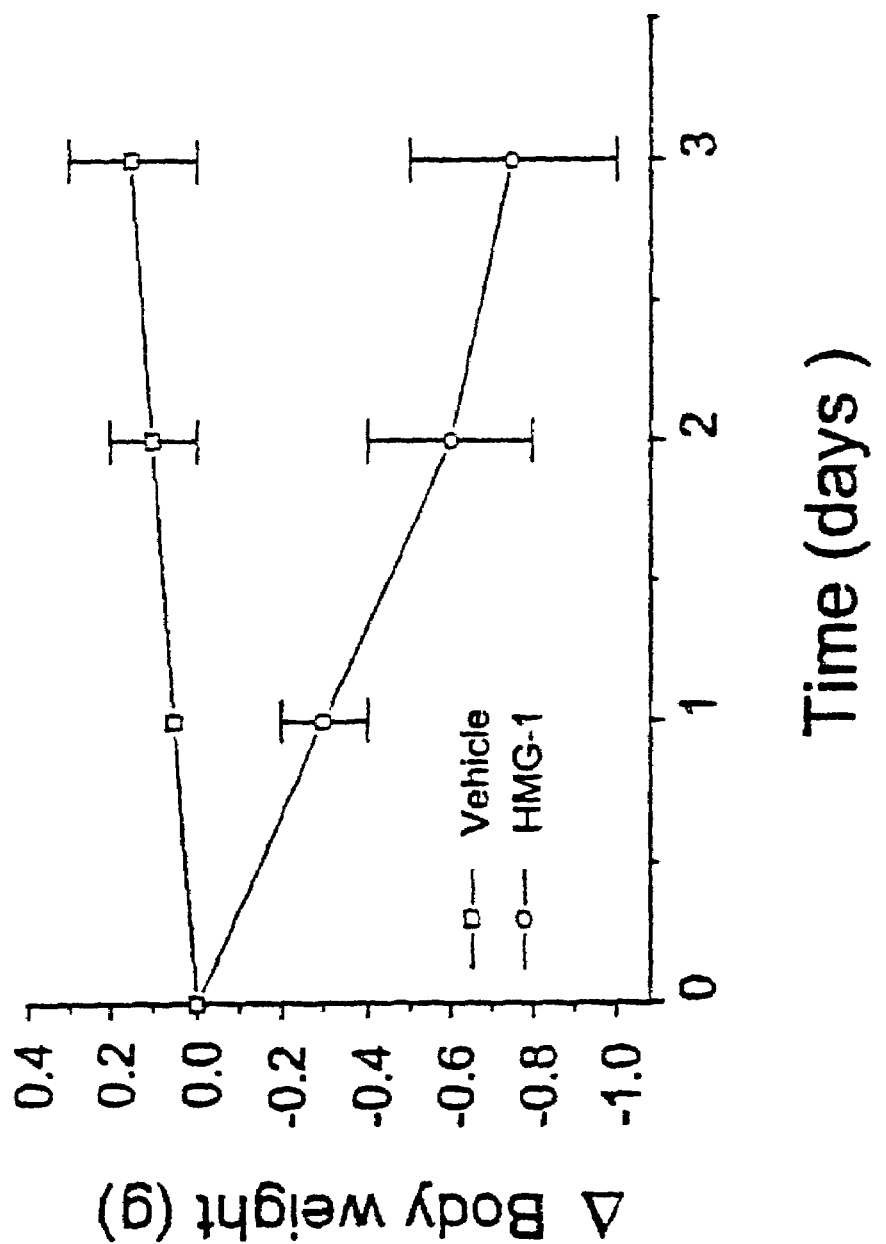
FIG. 4 shows that HMG1 caused body weight loss in mice. Purified HMG1 was administered intraperitoneally to mice at 100 μg/mouse/day for three days, and body weight was monitored.

Repetitive administration of recombinant gene product of the HMG1 gene (100 μg/mouse/day) caused significant body weight loss (FIG. 4) in mice. Without limitation as to mechanism and without being bound by theory, these data are consistent with the hypothesis that HMG1 acts as a feed-forward stimulator of the pro-inflammatory cascade under both in vitro and in vivo conditions. These in vivo data in a predictive model of weight loss also provide predictive evidence that a pharmaceutical formulation comprising HMG1, or a therapeutically active fragment thereof, is an effective weight loss therapy.

EXAMPLE 9

In vivo Sources of HMG1

Serum HMG1 levels in hypophysectomized versus control rats also were measured by quantitation of Western blot intensities as described above. There were significantly higher HMG 1 levels within 12 hours after endotoxic challenge (LPS at 1.0 mg/kg) in hypophysectomizid rats (approx. 75 ng/ml) as compared to controls (approx. 25 ng/ml). These results indicate that pituicytes are not the major source of serum HMG1 levels and that macrophages may play a quantitatively more important role.

EXAMPLE 10

Figure 7:
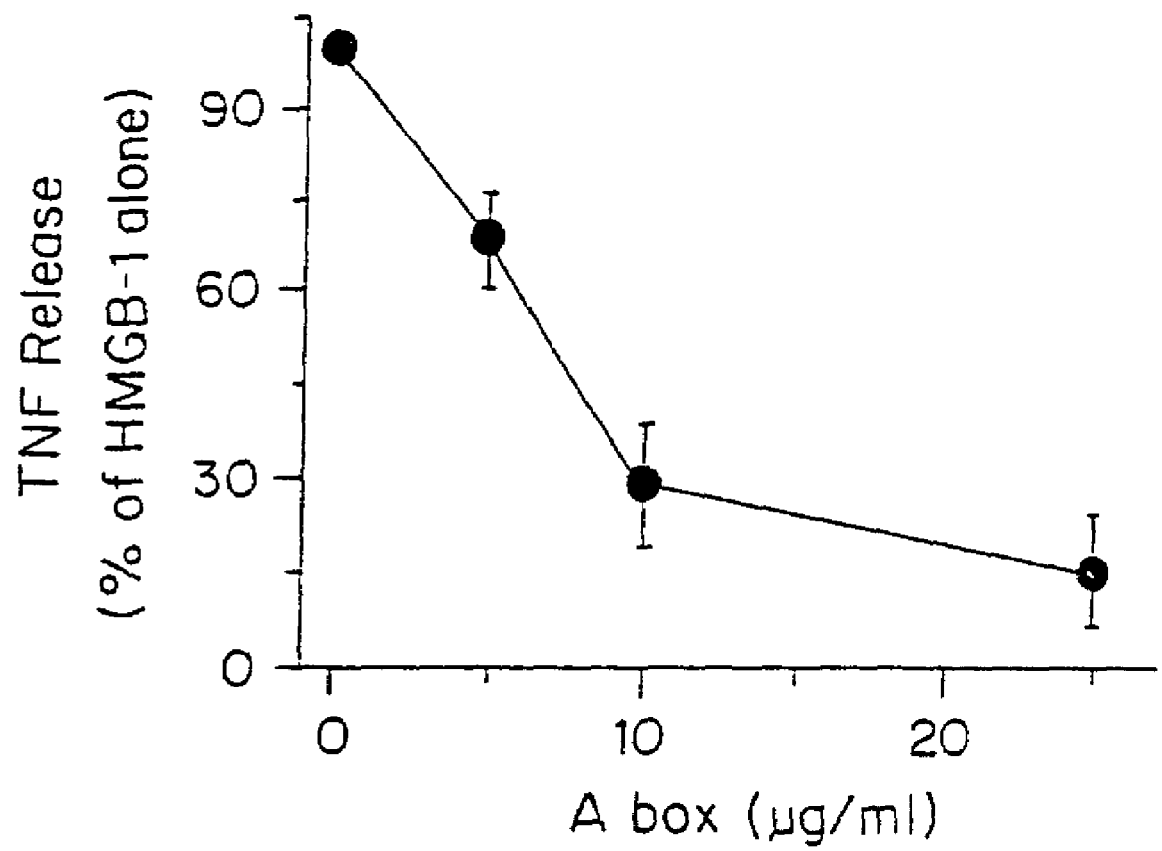
FIG. 7 is a graph of the effect of 0 μg/ml, 5 μg/ml, 10 μg/ml, or 25 μg/ml of HMG1 A box protein on the release of TNF (as a percent of HMG1 mediated TNF release alone) from RAW 264.7 cells.

HMG1 A Box Polypeptide Antagonizes HMG1 Induced Cytokine Activity in a Dose Dependent Manner An HMG1 fragment, termed the "A box" (a polypeptide fragment of HMG1 having the amino acid sequence: pdasvnfsef skkcserwkt msakekgkfe dmakadkary eremktyipp kget (SEQ ID NO: 6)), does not stimulate TNF activity the extent that the full-length HMG1 protein does. Weak agonists are by definition antagonists; and therefore, the ability of HMG1 A box to act as an antagonist of HMG1 activity was evaluated. This study was carried out as follows. Sub-confluent RAW 264.7 cells in 24-well dishes were treated with HMG1 (1 μg/ml) and 0, 5, 10, or 25 μg/ml of A box for 16 hours in Opti-MEM I medium in the presence of polymyxin B (100 units/ml). The TNF-stimulating activity (assayed using an L929 cytotoxicity assay described by Bianchi et al., *Journal of Experimental Medicine* 183: 927–936, 1996) in the sample receiving no A box was expressed as 100%, and the inhibition by A box was expressed as percent of HMG1 alone. The results of the effect of A box on TNF release from RAW 264.7 cells is shown in FIG. 7. As shown in FIG. 7, the A box dose-dependently inhibited HMG1 induced TNF release with an apparent $EC_{50}$ of approximately 7.5 μg/ml. Data in FIG. 7 are presented as mean SD (n=2–3 independent experiments).

EXAMPLE 11

HMG1 A Box Polypeptide Inhibits Full Length HMG1 Cytokine Activity

Figure 8:
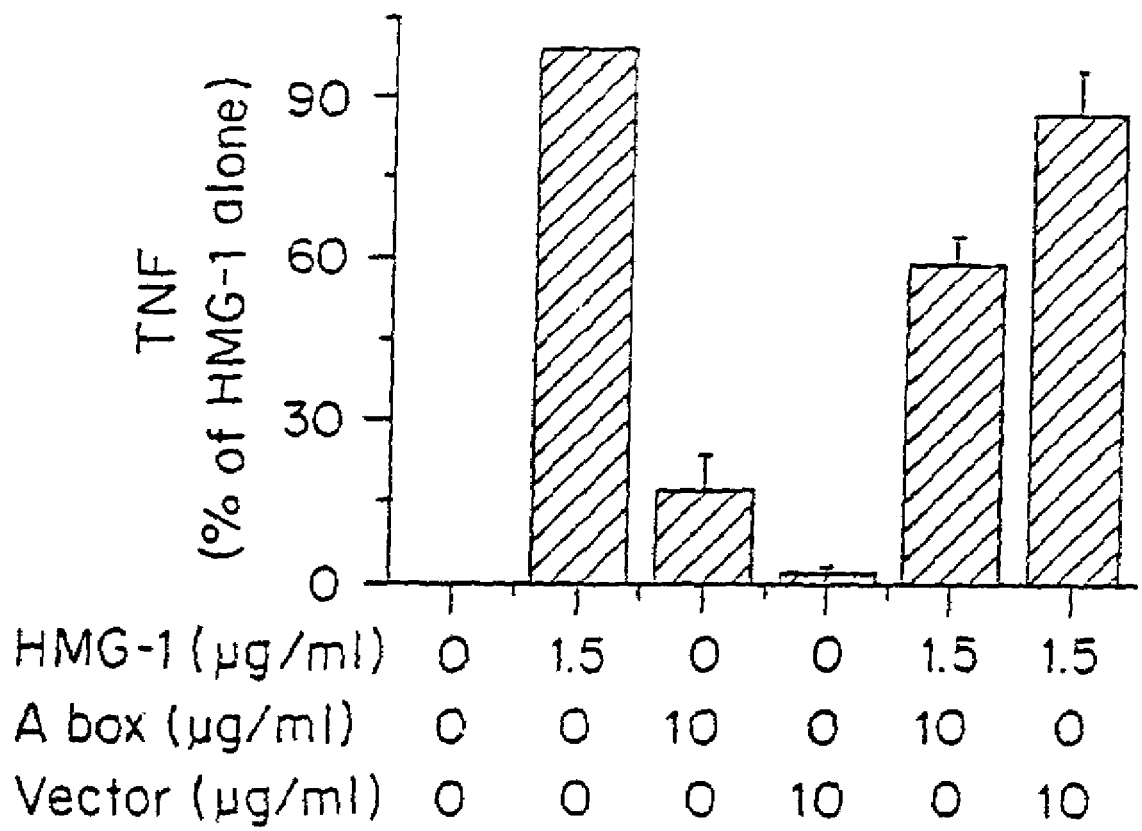
FIG. 8 is a histogram of the effect of HMG1 (0 or 1.5 µg/ml), HMG1 A box (0 or 10 µg/ml), or vector (0 or 10 µg/ml), alone, or in combination on the release of TNF (as a percent of HMG1 mediated TNT release alone) from RAW 264.7 cells.

Antagonism of full length HMG1 activity by an HMG1 A box polypeptide or a GST tag (vector control) was also determined by measuring TNF release from RAW 264.7 macrophage cultures stimulated by co-addition of HMG1 A box polypeptide with full length HMG1. RAW 264.7 macrophage cells (ATCC) were seeded into 24-well tissue culture plates and used at 90% confluence. The cells were treated with HMG1 alone, or in combination with A box polypeptide for 16 hours in Optimum I medium (Life Technologies, Grand Island, N.Y.) in the presence of polymyxin B (100 units/ml, Sigma, St. Louis, Mo.) and supernatants were collected for TNF measurement (mouse ELISA kit from R&D System Inc, Minneapolis, Minn.). TNF-inducing activity was expressed as a percentage of the activity achieved with HMG-1 alone. The results of these studies are shown in FIG. 8. FIG. 8 is a histogram of the effect of HMG1 alone, A box polypeptide alone, Vector (control) alone, HMG1 in combination with A box polypeptide, and HMG1 in combination with vector. As shown in FIG. 8, HMG1 A box polypeptide significantly attenuated the TNF stimulating activity of full length HMG1.

What is claimed is:

1. A method for treating a cardiovascular condition characterized by activation of the inflammatory cytokine cascade, comprising administering an effective amount of an antibody that specifically binds an HMG1 protein or an antigenic fragment thereof, wherein said antibody inhibits HMG1-mediated activation of the inflammatory cytokine cascade.

2. The method of claim 1, wherein said antibody is a polyclonal antibody.

3. The method of claim 1, wherein said antibody is a monoclonal antibody.

4. The method of claim 1, wherein said antibody is a chimeric antibody.

5. The method of claim 1, wherein said antibody is a single chain antibody.

6. The method of claim 1, wherein said antibody is a human antibody.

7. The method of claim 1, wherein said antibody is a humanized antibody.

8. The method of claim 1, wherein said antibody can bind to a peptide consisting of the amino acid sequence GKGDPKKPRGKMSSC (SEQ ID NO:4).

9. A method for treating a cardiovascular condition characterized by activation of the inflammatory cytokine cascade, comprising administering a pharmaceutical composition comprising an effective amount of an antibody that specifically binds an HMG1 protein or an antigenic fragment thereof, wherein said antibody inhibits HMG1-mediated activation of the inflammatory cytokine cascade.

10. A method for treating a cardiovascular condition characterized by activation of the inflammatory cytokine cascade, comprising administering an effective amount of an antibody fragment that specifically binds an HMG1 protein or an antigenic fragment thereof, wherein said antibody fragment inhibits HMG1-mediated activation of the inflammatory cytokine cascade.

11. The method of claim 10, wherein said antibody fragment is an antibody fragment of a polyclonal antibody.

12. The method of claim 10, wherein said antibody fragment is an antibody fragment of a mono clonal antibody.

13. The method of claim 10, wherein said antibody fragment is an antibody fragment of a chimeric antibody.

14. The method of claim 10, wherein said antibody fragment is an antibody fragment of a single chain antibody.

15. The method of claim 10, wherein said antibody fragment is an antibody fragment of a human antibody.

16. The method of claim 10, wherein said antibody fragment is an antibody fragment of a humanized antibody.

17. The method of claim 10, wherein said antibody fragment is an Fab fragment.

18. The method of claim 10, wherein said antibody fragment can bind to a peptide consisting of the amino acid sequence GKGDPKKPRGKMSSC (SEQ ID NO:4).

19. A method for treating a cardiovascular condition characterized by activation of the inflammatory cytokine cascade, comprising administering a pharmaceutical composition comprising an effective amount of an antibody fragment that specifically binds an HMG1 protein or an antigenic fragment thereof, wherein said antibody fragment inhibits HMG1-mediated activation of the inflammatory cytokine cascade.

* * * * *

SEQUENCE LISTING

```
<160> NUMBER OF SEQ ID NOS: 6

<210> SEQ ID NO 1
<211> LENGTH: 14
<212> TYPE: PRT
<213> ORGANISM: Homo sapiens
```

```
<400> SEQUENCE: 1

Gly Lys Gly Asp Pro Lys Lys Pro Arg Gly Lys Met Ser Ser
1               5                   10

<210> SEQ ID NO 2
<211> LENGTH: 42
<212> TYPE: DNA
<213> ORGANISM: Artificial Sequence
<220> FEATURE:
<223> OTHER INFORMATION: PCR primer

<400> SEQUENCE: 2
cccgcggatc catcgaggga aggatgggca aaggagatcc ta                42

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
cccgcaagct tattcatcat catcatcttc t                            31

<210> SEQ ID NO 4
<211> LENGTH: 15
<212> TYPE: PRT
<213> ORGANISM: Artificial Sequence
<220> FEATURE:
<223> OTHER INFORMATION: antigen

<400> SEQUENCE: 4

Gly Lys Gly Asp Pro Lys Lys Pro Arg Gly Lys Met Ser Ser Cys
1               5                   10                  15

<210> SEQ ID NO 5
<211> LENGTH: 42
<212> TYPE: DNA
<213> ORGANISM: Artificial Sequence
<220> FEATURE:
<223> OTHER INFORMATION: antisense oligonucleotide

<400> SEQUENCE: 5
gaggaaaaat aactaaacat gggcaaagga gatcctaaga ag                42

<210> SEQ ID NO 6
<211> LENGTH: 54
<212> TYPE: PRT
<213> ORGANISM: Homo Sapiens

<400> SEQUENCE: 6

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
                20                  25                  30

Ala Lys Ala Asp Lys Ala Arg Tyr Glu Arg Glu Met Lys Thr Tyr Ile
            35                  40                  45

Pro Pro Lys Gly Glu Thr
    50
```